US009556108B2

(12) United States Patent
Liao et al.

(10) Patent No.: US 9,556,108 B2
(45) Date of Patent: Jan. 31, 2017

(54) PROCESS FOR PREPARING SUBSTITUTED PHENYLALKANES

(71) Applicant: Mallinckrodt LLC, Hazelwood, MO (US)

(72) Inventors: Subo Liao, Hazelwood, MO (US); Joseph McClurg, Hazelwood, MO (US); Bobby Trawick, Hazelwood, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 14/796,069

(22) Filed: Jul. 10, 2015

(65) Prior Publication Data
US 2016/0009635 A1  Jan. 14, 2016

Related U.S. Application Data

(60) Provisional application No. 62/155,913, filed on May 1, 2015, provisional application No. 62/022,815, filed on Jul. 10, 2014.

(51) Int. Cl.
| C07C 213/02 | (2006.01) |
| C07C 213/08 | (2006.01) |
| C07C 45/62 | (2006.01) |
| C07C 45/68 | (2006.01) |
| C07C 45/69 | (2006.01) |
| C07C 45/65 | (2006.01) |

(52) U.S. Cl.
CPC ............ *C07C 213/08* (2013.01); *C07C 45/62* (2013.01); *C07C 45/65* (2013.01); *C07C 45/68* (2013.01); *C07C 45/69* (2013.01); *C07C 213/02* (2013.01); *C07B 2200/07* (2013.01)

(58) Field of Classification Search
CPC combination set(s) only.
See application file for complete search history.

(56) References Cited

U.S. PATENT DOCUMENTS

| 4,113,781 | A | 9/1978 | Aquila |
| 6,248,737 | B1 | 6/2001 | Buschmann |
| 6,344,558 | B1 | 2/2002 | Buschmann |
| 7,321,038 | B2 | 1/2008 | Wang |
| 7,323,565 | B2 | 1/2008 | Wang |
| 7,399,858 | B2 | 7/2008 | Wang |
| 7,608,709 | B2 | 10/2009 | Imamoto |
| 2009/0326271 | A1 | 12/2009 | Hell |
| 2010/0317683 | A1 | 12/2010 | Grote |
| 2011/0105748 | A1 | 5/2011 | Bhuniya |
| 2011/0230620 | A1 | 9/2011 | Tunge |
| 2011/0306793 | A1 | 12/2011 | Buschmann et al. |
| 2012/0142934 | A1 | 6/2012 | Cheng |
| 2013/0060065 | A1* | 3/2013 | Jagusch ............... C07C 213/08 564/383 |
| 2013/0310555 | A1 | 11/2013 | Chong |

FOREIGN PATENT DOCUMENTS

| JP | 2013221025 | 10/2013 |
| WO | 0181303 A1 | 11/2001 |
| WO | 2008012046 A1 | 1/2008 |
| WO | 2011026314 A1 | 3/2011 |
| WO | 2011067386 A2 | 6/2011 |
| WO | 2011080736 A1 | 7/2011 |
| WO | 2011107876 A2 | 9/2011 |
| WO | 2013174947 A1 | 11/2013 |
| WO | 2016007823 A1 | 1/2016 |

OTHER PUBLICATIONS

"Chiral Diene and NHC Ligands for Asymmetric Catalysis," Aldrichimica Acta, 2009, vol. 42, No. 2, 28 pp.
Apodaca et al., "Direct Reductive Amination of Aldehydes and Ketones Using Phenylsilane: Catalysis by Dibutyltin Dichloride," Org. Letters, 2001, 3(11), 1745-1748.
Bugarin et al., "Efficient, direct a-methylenation of carbonyls mediated by diisopropylammonium trifluoroacetatew," Chem. Commun., 2010, 46, 1715-1717.
Dousa et al., "Fundamental study of enantioselective HPLC separation of tapentadol enantiomers using cellulose-based chiral stationary phase in normal phase mode," J. Pharma. Biomed. Anal., 2013, 74, 111-116.
Erkkila et al., "Mild Organocatalytic r-Methylenation of Aldehydes," J. Org. Chem, 2006, 71, 2538-2541.
Gomez et al., "The Reductive Amination of Aldehydes and Ketones and the Hydrogenation of Nitriles: Mechanistic Aspects and Selectivity Control," Adv. Synth. Catal., 2002, 344(10), 1037-1057.
Hayashi et al., "Asymmetric 1,4-Addition of Arylboronic Acids to ,-Unsaturated Aldehydes Catalyzed by a Chiral Diene-Rhodium Complex," Chem. Lett., 2005, 34(11), 1480-1481.
Itooka et al., "Rhodium-Catalyzed 1,4-Addition of Arylboronic Acids to α,β-Unsaturated Carbonyl Compounds: Large Accelerating Effects of Bases and Ligands", J. Org. Chem., 2003, 68(15), 6000-6004.
McCarthy et al., "Axially chiral bidentate ligands in asymmetric catalysis," Tetrahedron, 2001, 57(18), 3809-3844.
Paquin et al., "Asymmetric Synthesis of 3,3-Diarylpropanals with Chiral Diene-Rhodium Catalysts," J. Am. Chem. Soc., 2005, 127, 10850-10851.
Paquin et al., "Catalytic Asymmetric Synthesis with Rh-Diene Complexes: 1,4-Addition of Arylboronic Acids to Unsaturated Esters," Org. Lett., 2005, 7(17), 3821-3824.
Pihko et al., "Mild Organocatalytic α-Methylenation of Aldehydes," J. Org. Chem. 2006, 71, 2538-2541.
Shintani et al., "Tuning the Chiral Environment of C2-Symmetric Diene Ligands: Development of 3,7-Disubstituted Bicyclo[3.3.1]nona-2,6-dienes," J. Org. Chem., 2009, 74, 869-873.
Smit et al., "Tuning the Chiral Environment of C2-Symmetric Diene Ligands: Development of 3,7-Disubstituted Bicyclo [3.3.1]nona-2,6-dienes," J. Org. Chem., 2008, 73, 9482-9485.

(Continued)

*Primary Examiner* — Clinton Brooks

(57) ABSTRACT

The invention provides methods for preparing substituted phenylalkanes. In particular, the processes comprise reacting a phenyl boronic compound with an α-β unsaturated carbonyl-containing compound via an asymmetric 1,4-addition reaction. The processes may be useful in the synthesis of tapentadol.

20 Claims, No Drawings

(56) References Cited

OTHER PUBLICATIONS

Tang et al., "New Chiral Phosphorous Ligands for Enantioselective Hydrogenation," Chemical Reviews, 2003, 103, 3029-3069.
Tripathi et al., "Recent Development on Catalytic Reductive Amination and Applications," Curr. Org. Chem., 2008, 12 (13), 1093-1115.
Uma et al., "Transposition of Allylic Alcohols into Carbonyl Compounds Mediated by Transition Metal Complexes," Chem. Rev., 2003, 103: 27-51.
Williams et al., "A One-Pot Process for the Enantioselective Synthesis of Amines via Reductive Amination under Transfer Hydrogenation Conditions," Org. Letters, 2003, 5(22), 4227-4230.
Zhang et al., "Practical and enantioselective synthesis of tapentadol." Tetrahedron: Asymmetry, 2012, 23(8), 577-582.
International Search Report and Written Opinion dated Oct. 13, 2015 of related International application No. PCT/US15/039884, 9 pp.

\* cited by examiner

PROCESS FOR PREPARING SUBSTITUTED PHENYLALKANES

CROSS-REFERENCE TO RELATED APPLICATIONS

This application claims the priority of U.S. Provisional Application Ser. No. 62/155,913, filed May 1, 2015, and U.S. Provisional Application Ser. No. 62/022,815, filed Jul. 10, 2014, the disclosure of each is hereby incorporated by reference in its entirety.

FIELD OF THE INVENTION

The present disclosure generally relates to the synthesis of substituted phenylalkanes via a catalytic asymmetric 1,4-addition reaction.

BACKGROUND OF THE INVENTION

Tapentadol (i.e., 3-[(1R,2R)-3-(dimethyamino)-1-ethyl-2-methylpropyl]phenol) is a small organic molecule that is used as an analgesic. Tapentadol is known to have a dual mechanism of action as an agonist of the μ-opioid receptor and also as a norepinephrine (NE) reuptake inhibitor (NRI) for improved analgesic efficacy especially in chronic or neuropathic pain disorders.

Several different routes for preparing tapentadol have been reported. A typical method is to produce a racemic mixture of intermediates that must be separated by chiral chromatographic separation or by chiral resolution. The separation of chiral compounds, however, can be technically challenging, time consuming, or both. What is needed, therefore, is a process for preparing tapentadol that does not require chiral separation or chiral resolution, but rather relies on a direct asymmetric synthesis of chiral compounds. Such an enantioselective synthesis process would facilitate the production of tapentadol by reducing costs and saving time.

SUMMARY OF THE INVENTION

Provided herein are processes for preparing chiral substituted phenylalkanes via catalytic asymmetric 1,4-addition reactions.

One aspect of the present disclosure provides a process for producing a compound of Formula (VI). The process comprises contacting a compound of Formula (I) with a compound of Formula (VIII) in the presence of a transition metal catalyst and a chiral ligand to form a compound of Formula (IX); contacting the compound of Formula (IX) with a compound of Formula (X) to form a compound of Formula (V); and contacting the compound of Formula (V) with an O-dealkylating agent to form the compound of Formula (VI) according to the general scheme:

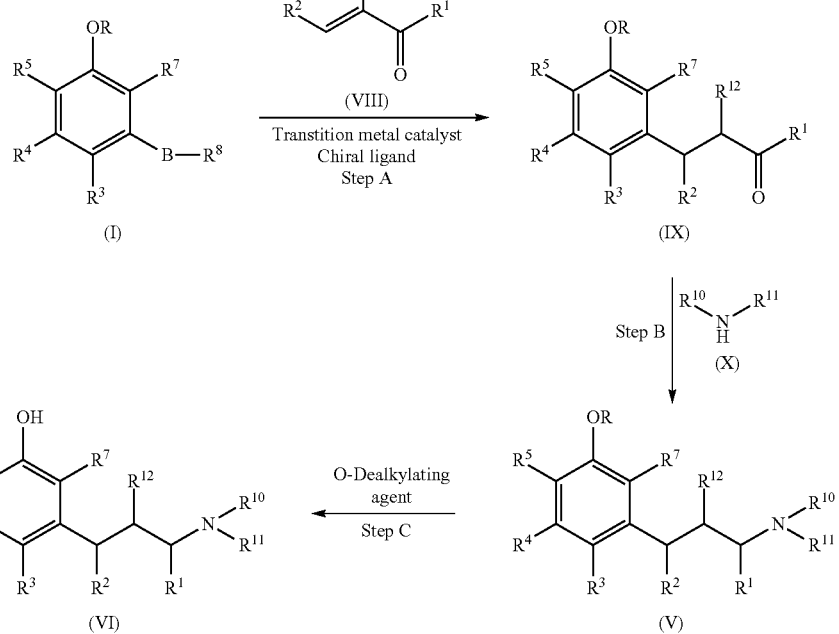

wherein:

R is alkyl or alkyl substituted with other than aryl;

$R^1$ is hydrogen, alkyl, or substituted alkyl;

$R^2$ is hydrocarbyl or substituted hydrocarbyl;

$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl;

$R^8$ is

—O—$(CR^{13}R^{14})_n$—O—, or trihalo;

$R^{10}$ and $R^{11}$ are independently hydrocarbyl, substituted hydrocarbyl, or $R^{10}$ and $R^{11}$ together may form a ring or ring system selected from carbocyclic, heterocyclic, aryl, heteroaryl, or combinations thereof;

$R^{12}$ is hydrocarbyl or substituted hydrocarbyl;

$R^{13}$ and $R^{14}$ are independently hydrogen, hydrocarbyl, substituted hydrocarbyl, or boron containing moiety;

$R^{20}$ and $R^{21}$ are independently hydrogen, hydrocarbyl, or substituted hydrocarbyl; and n is an integer of 1 or greater.

Other features and iterations of the disclosure are described in more detail below.

DETAILED DESCRIPTION OF THE INVENTION

The present disclosure provides concise processes for preparing a substituted phenylalkane compound. In general, the processes comprise a catalytic asymmetric 1,4-addition reaction of an unsubstituted α,β-unsaturated carbonyl-containing compound with a phenyl boronic compound. Methylenyl addition, reduction, reductive amination, and then phenolic demethylation provide a concise route to the substituted phenylalkane compound. Surprisingly, these reaction steps have been found useful in the total synthesis of tapentadol.

Using a α substituted α,β-unsaturated carbonyl compound, the catalytic asymmetric 1,4-addition reaction with a phenyl boronic compound then provides advantages over other conventional methods in its yield and selectivity. As an improvement, a reduction in two synthetic steps to reach tapentadol was achieved.

(I) A 5-Step Process for the Preparation of a Compound of Formula (VI)

One aspect of the present disclosure provides a process for preparing a compound of Formula (VI). The process comprises contacting a compound of Formula (I) with a compound of Formula (VII) in the presence of a transition metal catalyst and a chiral ligand to form a compound of Formula (II); contacting the compound of Formula (II) with a methylenyl addition agent to form a compound of Formula (III); contacting the compound of Formula (III) with a hydrogen source to form a compound of Formula (IV); contacting the compound of Formula (IV) with a secondary amine having Formula (X) to form a compound of Formula (V); and contacting the compound of Formula (V) with an O-dealkylating agent to form the compound of Formula (VI) according to Reaction Scheme 1:

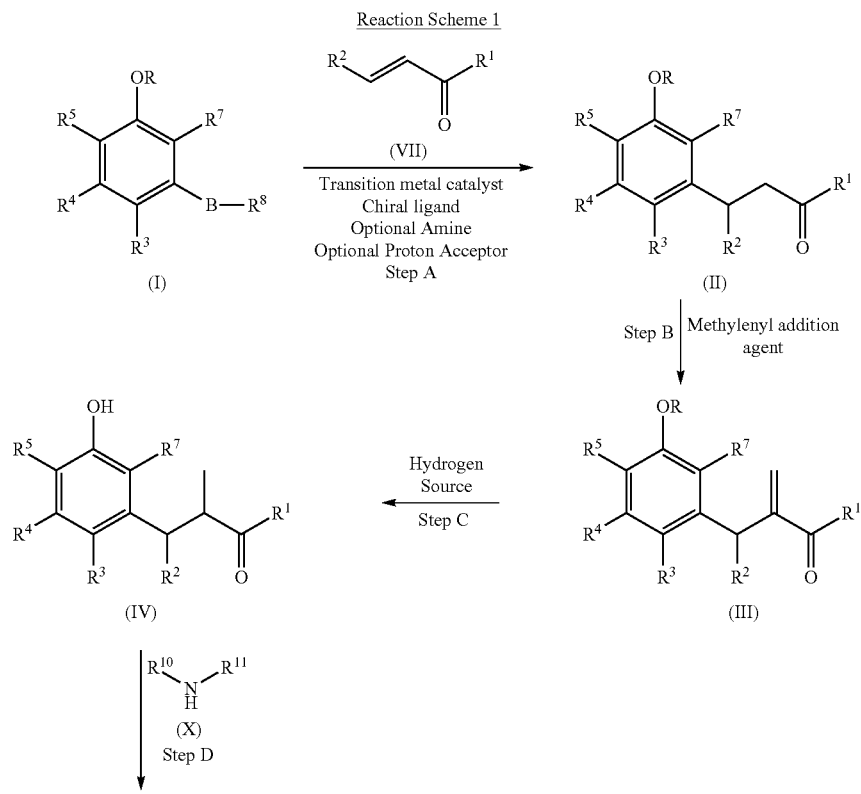

Reaction Scheme 1

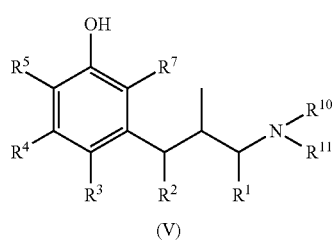

(V)

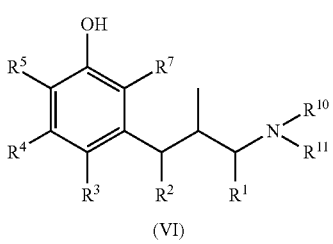

(VI)

wherein:
R is alkyl or alkyl substituted with other than aryl;
$R^1$ is hydrogen, alkyl, or substituted alkyl;
$R^2$ is chosen from hydrocarbyl and substituted hydrocarbyl;
$R^3$, $R^4$, $R^5$, and $R^7$ are independently chosen from hydrogen, $OR^{20}$, $NR^{20}R^{21}$, $SR^{20}R^{21}$, halo, hydrocarbyl, and substituted hydrocarbyl;
$R^8$ is

—O—$(CR^{13}R^{14})_n$—O—, or trihalo;
$R^{10}$ and $R^{11}$ are independently chosen from hydrocarbyl and substituted hydrocarbyl;
$R^{13}$ and $R^{14}$ are independently hydrogen, hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{20}$ and $R^{21}$ are independently chosen from hydrogen, hydrocarbyl, and substituted hydrocarbyl; and
n is an integer of 1 or greater.

In general, R is alkyl or alkyl substituted with a substituent other than aryl. The alkyl may be linear, branched, or cyclic. In one embodiment, R may be $C_1$-$C_{10}$ alkyl or substituted $C_1$-$C_{10}$ alkyl. In certain embodiments, R may be methyl, ethyl, propyl, isopropyl, butyl, tertbutyl, pentyl, or hexyl. In specific embodiments, R may be methyl.

In some embodiments, $R^1$ may be hydrogen, alkyl, substituted alkyl, aryl, or substituted aryl. In other embodiments, $R^1$ may be hydrogen, $C_1$-$C_{10}$ alkyl, or substituted $C_1$-$C_{10}$ alkyl, wherein alkyl may be linear, branched, or cyclic. In specific embodiments, $R^1$ may be hydrogen.

In other embodiments, $R^2$ may be alkyl, substituted alkyl, alkenyl, substituted alkenyl, alkynyl, substituted alkynyl, aryl, substituted aryl, alkylaryl, or substituted alkylaryl. In certain embodiments, $R^2$ may be $C_1$-$C_{10}$ alkyl or substituted $C_1$-$C_{10}$ alkyl. In some embodiments, $R^2$ may be methyl, ethyl, propyl, isopropyl, butyl, tertbutyl, pentyl, or hexyl. In specific embodiments, $R^2$ may ethyl.

In some embodiments, $R^3$, $R^4$, $R^5$, and $R^7$ may be independently hydrogen, alkyl, substituted alkyl, hydroxyl, alkoxy, substituted alkoxy, aryl, substituted aryl, alkylaryl, or substituted alkylaryl. In embodiments in which $R^3$, $R^4$, $R^5$, or $R^7$ independently may be $OR^{20}$, $NR^{20}R^{21}$, $SR^{20}R^{21}$, $R^{20}$ and $R^{21}$ independently are hydrogen, alkyl, substituted alkyl, aryl, or substituted aryl. In specific embodiments, each of $R^3$, $R^4$, $R^5$, and $R^7$ is hydrogen.

In certain embodiments, $R^8$ may be

wherein $R^{13}$ and $R^{14}$ are independently hydrogen, alky, substituted alkyl, aryl, substituted aryl, alkylaryl, substituted alkylaryl, or organoborane. In one iteration of this embodiment, each of $R^{13}$ and $R^{14}$ is hydrogen. In other embodiments, $R^8$ may be —O—$(CR^{13}R^{14})_n$—O—, wherein $R^{13}$ and $R^{14}$ are independently hydrogen, alkyl, substituted alkyl, aryl, substituted aryl, alkylaryl, substituted alkylaryl, or organoborane, and n is 1 or greater. In one iteration of this embodiments, each of $R^{13}$ and $R^{14}$ is methyl and n is 2. In still another embodiment, $R^8$ may be trihalo, such as, e.g., trifluoro.

In further embodiments, $R^{10}$ and $R^{11}$ independently may be $C_1$-$C_{10}$ alkyl or substituted $C_1$-$C_{10}$ alkyl, wherein alkyl is linear, branched, or cyclic. In certain embodiments, $R^{10}$ and $R^{11}$ independently may be methyl, ethyl, propyl, isopropyl, butyl, tertbutyl, pentyl, or hexyl. In specific embodiments, each of $R^{10}$ and $R^{11}$ may be methyl.

In exemplary embodiments, R may be methyl; $R^1$ may be hydrogen; $R^2$ may be ethyl; each of $R^3$, $R^4$, $R^5$, and $R^7$ may be hydrogen; and each of $R^{10}$ and $R^{11}$ may be methyl.

(a) Step A of the 5-Step Process

Step A involves contacting a phenyl boronic compound of Formula (I) with a compound of Formula (VII) in the presence of a transition metal catalyst and a chiral ligand to form a compound of Formula (II). Contact between the phenyl boronic compound of Formula (I) and the compound of Formula (VII) during step A of the process entails an asymmetric 1,4-addition reaction.

(i) Phenyl Boronic Compound

The phenyl boronic acid comprising Formula (I) is detailed above. In some embodiments, R may be alkyl, each of $R^3$, $R^4$, $R^5$, and $R^7$ may be hydrogen, alkyl, or substituted alkyl, and $R^{13}$ and $R^{14}$, if present, may be hydrogen or alkyl. In certain embodiments, R may be alkyl, each of $R^3$, $R^4$, $R^5$, and $R^7$ may be hydrogen, and $R^{13}$ and $R^{14}$, if present, may be hydrogen or alkyl. In preferred embodiments in which R is methyl and each of $R^3$, $R^4$, $R^5$, and $R^7$ is hydrogen, the compound of Formula (I) may be m-methoxyphenylboronic acid, 3-methoxyphenyl trifluoroborate, and 3-methoxyphenylboronic acid pinacol ester, 3-methoxyphenylboronic ester, or an acceptable salt thereof. Also, a compound of Formula (I) may be derived from mono, bis, or tris substituted 3-methoxyphenylboroxine, or an acceptable salt thereof.

(ii) α/β-Unsaturated Carbonyl Compound

The α,β-unsaturated carbonyl compound of Formula (VII) is detailed above. In some embodiments, $R^1$ and $R^2$ may be hydrogen, alkyl, or substituted alkyl. In certain embodiments, $R^1$ may be hydrogen and $R^2$ may be alkyl or substituted alkyl. In preferred embodiments in which $R^1$ is hydrogen and $R^2$ is ethyl, the compound may be trans-2-methyl-2-pentenal.

In general, the molar ratio of the compound of Formula (I) to the compound of Formula (VII) may range from about 1:0.5 to about 1:2.0. In various embodiments, the molar ratio of the compound of Formula (I) to the compound of Formula (VII) may range from about 1:0.5 to about 1:0.6, 1:0.6 to about 1:0.7, 1:0.7 to about 1:0.8, 1:0.8 to about 1:0.9, from about 1:0.9 to 1:1, from about 1:1 to about 1:1.2, from about 1:1.2 to about 1:1.4, from about 1:1.4 to about 1:1.6, from about 1:1.6 to about 1:1.8, or from about 1:1.8 to about 1:2. In one exemplary embodiment, the molar ratio of the compound of Formula (I) to the compound of Formula (VII) may range from about 1:0.8 to about 1:1.2. In another exemplary embodiment, the molar ratio of the compound of Formula (I) to the compound of Formula (VII) may be about 1:1.

(iii) Transition Metal Catalyst

A wide variety of transition metal catalysts may be used in the process to catalyze the 1,4-addition of step A. As used herein, the term "transition metal catalyst" refers to a transition metal element, transition metal salt, or a transition metal complex. In some embodiments, the transition metal may be iridium, iron, nickel, osmium, palladium, platinum, ruthenium, or rhodium. In one exemplary embodiment, the transition metal may be ruthenium, iridium, or rhodium. A skilled artisan appreciates that the oxidation state of transition metal may vary, and may be, for example, (0), (I), (II), (III), (IV), (V), (VI) or (VII). For example, non-limiting examples of suitable transition metals include ruthenium (II), ruthenium (III), ruthenium (IV), osmium (II), osmium (III), osmium (IV), rhodium (I), rhodium (III), iridium (III), iridium (IV), palladium (II), palladium (IV), platinum (II), and platinum (IV). In an exemplary embodiment the transition metal may be rhodium (I).

In some embodiments, the transition metal catalyst may be the transition metal element itself. For example, the transition metal element may be a powder or a sponge, such as, e.g., ruthenium powder, rhodium powder, ruthenium sponge, rhodium sponge, palladium sponge, and so forth. Alternatively, the transition metal element may be rhodium black, ruthenium black, palladium black, etc. In still other embodiments, the transition metal element may be immobilized on a solid surface or support. Suitable examples include, but are not limited to, ruthenium on carbon, rhodium on carbon, palladium on carbon, ruthenium on alumina, rhodium on alumina, platinum on alumina, palladium on alumina, rhodium on silica, palladium on silica, palladium on charcoal, palladium on pumice, and so forth.

In other embodiments, the transition metal catalyst may be a transition metal salt. Non-limiting examples of suitable salts include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, trifluoromethanesulfonates, tri methylacetates, tosylates, and combinations thereof. Non-limiting examples of suitable transition metal salts include $RuCl_3$, $RuBr_3$, $Ru(CF_3SO_3)_2$, $Ru_2(SO_4)_3$, $Ru(NO_3)_3$, $Ru(OAc)_3$, $PdCl_2$, $Pd(OAc)_2$, $RhCl_3$, $RhBr_3$, $Rh_2(SO_4)_3$, $(Rh(CO_2)Cl)_2$, $Rh_2(SO_4)_3$, $Rh_2(OAC)_4$, $IrCl_3$, and $OsCl_3$. The transition metal salt may be soluble (i.e., homogeneous). Alternatively, the transition metal salt may be immobilized on a solid support (i.e., heterogeneous). The transition metal salt may be immobilized on the solid support via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

In further embodiments, the transition metal catalyst may be a transition metal complex. For example, the transition metal catalyst may be a rhodium complex, a palladium complex, or a ruthenium complex. In general, a transition metal complex comprises the transition metal and 4, 5, or 6 coordinate species with oxidation states ranging from 0 to 8. The complexes may be ionic, or the complexes may comprise covalently bound ligands and counter ions. Alternatively, the complexes may comprise a mixture of ionic and covalent bonds between the metal, ligand(s), and/or counter ion(s). The ligand may be monodentate or polydentate. Non-limiting examples of suitable ligands include arene ligands, olefin ligands, alkyne ligands, heterocycloalkyl ligands, heteroaryl ligands, alkyl ligands, cyclopentadienyl ligands, hydride ligands, amine ligands, carbonyl ligands, nitrogen donor ligands, phosphorous donor ligands, oxygen donor ligands, and so forth. The ligand may also be a solvent such as, e.g., DMSO, methanol, methylene chloride, tetrahydrofuran, acetone, ethanol, pyridine, or a tetraalkylammonia compound. Suitable counter ions include, but are not limited to, halides, $BF_4^-$, $PF_6^-$, $ClO_4^-$, $CHO_2^-$, $CF_3SO_3^-$, $CH_3CO_2^-$, $ArCO_2^-$, $CH_3SO_3^-$, p- tolyl$SO_3^-$, $HSO_4^-$, $H_2PO_4^-$, and hydrocarbyl anions. Numerous transition metal complexes are detailed in "Transposition of Allylic Alcohols into Carbonyl Compounds Mediated by Transition Metal Complexes" by Uma et al., Chem. Rev. 103: 27-51 (2003). The transition metal complex may be soluble (i.e., homogeneous). Alternatively, the transition metal complex may be immobilized on a solid support (i.e., heterogeneous). The transition metal complex may be immobilized on the solid support via noncovalent or covalent bonds. Examples of suitable solid supports are presented above.

Exemplary transition metal catalysts include, but are not limited to, $[RhCl(C_2H_4)_2]_2$, $[RuCl(C_2H_4)_2]_2$, $[PdCl(C_2H_4)_2]_2$, $[PtCl(C_2H_4)_2]_2$, $[RhBr(C_2H_4)_2]_2$, $[RuBr(C_2H_4)_2]_2$, $[PdBr(C_2H_4)_2]_2$, $[PtBr(C_2H_4)_2]_2$, (1,5-cyclooctadiene)bis(triphenylphosphine)rhodium(I) hexafluorophosphate, (acetylacetonato)(1,5-cyclooctadiene)rhodium(I), (acetylacetonato)(norbornadiene)rhodium(I), [1,4-bis(diphenylphosphino)butane](1,5-cyclooctadiene)rhodium(I) tetrafluoroborate, acetylacetonatobis(ethylene)rhodium(I), bicyclo[2.2.1]hepta-2,5-diene-rhodium(I) chloride, bis(1,5-cyclooctadiene)rhodium(I) tetrafluoroborate, bis(1,5-cyclooctadiene)rhodium(I) tetrakis[bis(3,5-trifluoromethyl) phenyl]borate, bis(1,5-cyclooctadiene)rhodium(I) trifluoromethanesulfonate, bis(acetonitrile)(1,5-cyclooctadiene)rhodium(I)tetrafluoroborate, bis(norbornadiene) rhodium(I) tetrafluoroborate, bis(triphenylphosphine)rhodium (I) carbonyl chloride, bis[rhodium(α,α,α',α'-tetramethyl-1, 3-benzenedipropionic acid)], chloro(1,5-hexadiene)rhodium (I), chlorobis(cyclooctene)rhodium(I), dicarbonyl (pentamethyl-cyclopentadienyl)rhodium(I), hydridotetrakis (triphenylphosphine)rhodium(I), hydroxy(cyclooctadiene) rhodium(I), methoxy(cyclooctadiene)rhodium(I), rhodium (II) heptafluorobutyrate, rhodium(II) hexanoate, rhodium(II) octanoate, rhodium(II) trifluoroacetate, rhodium(II) trimethylacetate, rhodium(II) triphenylacetate, rhodium(III) acetylacetonate, rhodium(III) phosphate, tris(triphenylphosphine)rhodium(I) carbonyl, tris(triphenylphosphine)rhodium(I), (2-methylallyl)palladium(II) chloride, (ethylenediamine)palladium(II) chloride, [1,2-bis (dicyclohexylphosphino)ethane]palladium(II) chloride, [2,6-bis[(di-1-piperidinylphosphino)amino]phenyl]palladium(II) chloride, 1,2-bis(phenylsulfinyl)ethane palladium (II) acetate, 1,4-bis(diphenylphosphino) butane-palladium (II) chloride, allylchloro[1,3-bis(2,4,6-trimethylphenyl) imidazol-2-ylidene]palladium(II), bis(benzonitrile) palladium(II) chloride, bis(dibenzylideneacetone) palladium (0), bis(triphenylphosphine)palladium(II) diacetate, bis (triphenylphosphine) palladium(II) dichloride, bis(tri-tert-butylphosphine)palladium(0), bis[(dicyclohexyl)(4-dimethylaminophenyl)phosphine]palladium(II) chloride, bromo(tri-tert-butylphosphine)palladium(I), chloro(2-dicyclohexylphosphino-2',4',6'-triisopropyl-1,1'-biphenyl)[2-(2-aminoethyl)phenyl)]palladium(II), chloro-(2-dicyclohexyl-phosphino-2',6'-diisopropoxy-1,1'-biphenyl)[2-(2-aminoethyl)phenyl]palladium(II), chloro[2-(dicyclohexylphosphino)-3,6-dimethoxy-2',4',6'-triisopropyl-1,1'-biphenyl][2-(2-aminoethyl)phenyl] palladium(II), chloro[2-(di-tert-butylphosphino)-2',4',6'-triisopropyl-1,1'-biphenyl][2-(2-aminoethyl)phenyl)] palladium(II), dichloro(1,5-cyclooctadiene) palladium(II), dichlorobis(tricyclohexylphosphine)palladium(II), di-μ-chlorobis[5-chloro-2-[(4-chlorophenyl)(hydroxyimino-κN) methyl]phenyl-κC]palladium, di-μ-chlorobis[5-hydroxy-2-[1-(hydroxyimino-κN)ethyl]phenyl-κC]palladium(II), N-methylimidazolium palladium(II), palladium(II) hexafluoroacetylacetonate, palladium(II)[1,3-bis(diphenylphosphino)propane]-bis(benzonitrile)-bis-tetrafluoroborate; tetrakis(acetonitrile)palladium(II), tetrakis(triphenylphosphine)palladium(0), tetrakis[triphenylphosphine]palladium (0), (1,5-cyclooctadiene)dimethylplatinum(II), (2,2'-bipyridine)dichloroplatinum(II), (N,N,N'-trimethylethylenediamine)platinum(II) chloride, ammonium hexachloroplatinate(IV), ammonium tetrachloroplatinate (II), bis(tri-tert-butylphosphine)platinum(0), chloro(2,2':6', 2"-terpyridine)platinum(II) chloride, cis-bis(acetonitrile)dichloroplatinum(II), cis-diammineplatinum(II) dichloride, cis-dichlorobis(diethyl sulfide)platinum(II), cis-dichlorobis (pyridine)platinum(II), cis-dichlorobis(triethylphosphine) platinum(II), cis-dichlorobis(triphenylphosphine) platinum (II), dibromo(1,5-cyclooctadiene)platinum(II), dichloro(1, 10-phenanthroline) platinum(II), dichloro(1,2-diaminocyclohexane)platinum(II), dichloro(1,5-cyclooctadiene)platinum(II), dichloro(2,2':6',2"-terpyridine) platinum(II) dihydrate, dichloro(dicyclopentadienyl) platinum(II), dichloro(ethylenediamine)platinum(II), dichloro(norbornadiene)platinum(II), dichlorobis(dimethyl sulfide)platinum(II), dichlorobis(ethylenediamine)platinum (II), ethylenebis(triphenylphosphine)platinum(0), oxalatobis (triethylphosphine)platinum(II), platinum(0)-1,3-divinyl-1, 1,3,3-tetramethyldisiloxane, platinum(0)-2,4,6,8-tetramethyl-2,4,6,8-tetravinylcyclo-tetrasiloxane, potassium hexachloroplatinate(IV), potassium tetrachloroplatinate(II), potassium tetracyanoplatinate(II), tetrakis(triphenylphosphine)platinum(0), trans-dichlorobis(triethylphosphine) platinum(II), trans-dichlorobis(triphenylphosphine) platinum(II), trimethyl(methylcyclopentadienyl)platinum(IV). In an exemplary embodiment, the transition metal catalyst may be [RhCl($C_2H_4$)$_2$]$_2$.

In other embodiments, the transition metal catalyst may be a complex comprising the transition metal and a tertiary phosphite, a tertiary phosphine, or a tertiary phosphine halide as detailed in U.S. Pat. Nos. 7,321,038, 7,399,858, and 7,323,565, each of which is incorporated herein with reference to the identity and synthesis of the transition metal catalyst. Non-limiting examples of phosphine containing complexes include (phosphine)$_x$PdCl$_2$, (PPh$_3$)$_4$Pd, RuCl$_2$ (PPh$_3$)$_3$, RuCl$_2$(PPh$_3$)$_4$, RuH$_2$(PPh$_3$)$_4$, and RhCl(PPh$_3$)$_3$. In yet another embodiment, transition metal catalyst may be a complex comprising the transition metal and an amine phosphine complex as described in U.S. Pat. No. 7,399,859, which is incorporated herein reference to the identity and synthesis of the transition metal catalyst. Suitable chiral phosphine ligands which may form transition metal complexes are listed below in section (I)(a)(ii).

The molar ratio of the compound of Formula (I) to the transition metal catalyst may vary depending, for example, on the nature of the catalyst. In general, the molar ratio of the compound of Formula (I) and the transition metal catalyst complex will range from about 1:0.0001 to about 1:0.05. In certain embodiments, the molar ratio of the compound of Formula (I) to the transition metal catalyst may range from about 1:0.0001 to about 1:0.001, from about 1:0.001 to about 1:0.005, from about 1:0.005 to about 1:0.025, or from about 1:0.025 to about 0.05. In one embodiment, the molar ratio of the compound of Formula (I) to the transition metal catalyst may range from about 1:0.0025 to about 1:0.01. In another embodiment, the molar ratio of the compound of Formula (I) to the transition metal catalyst may range from about 1:0.01 to about 1:0.02. In a further embodiment, the molar ratio of the compound of Formula (I) to the transition metal catalyst may be about 1:0.015.

(iv) Chiral Ligand

Chiral ligands may be any organic ligand that can complex with a catalytic metal and has at least one stable chiral center, and exemplarily two chiral centers. Phosphines, nitrogen-containing compounds and dienes are examples of classes of compounds that may function as chiral ligands.

Chiral phosphine ligands include, but are not limited to, (3,5-dioxa-4-phospha-cyclohepta[2,1-a;3,4-a']dinaphthalen-4-yl)dimethylamine (MONOPHOS), (3,5-dioxa-4-phospha-cyclohepta[2,1-a;3,4-a']dinaphthalen-4-yl)morpholine (MorfPhos), (3,5-dioxa-4-phospha-cyclohepta[2,1-a;3,4-a'] dinaphthalen-4-yl)piperidine (PipPhos), (5,6),(5',6')-bis(ethylenedioxy)-biphenyl-2,2'-diyl]-bis(diphenylphosphine) (Synphos), (6,6'-dimethyoxybiphenyl-2,2'-diyl)bis(diphenylphosphine) (BIPHEMP), 1-(2-dipheylphospino-1-naphthyl)isoquinoline (Quinap), 1-[(dinaphtho[2,1-d:1',2'-f][1,3, 2]dioxaphosphepin-4-yloxy)propan-2-yl]-3-phenylurea (UREAPhos), 1-tert-butoxycarbonyl-4-diphenylphosphino-2(diphenylphosphinomethyl)pyrrolidine (BPPM), 1,1'-di-t-butyl-[2,2']-diphospholane (TANGPHOS), 1,13-bis(diphenylphosphino)-7,8-dihydro-6H-dibenzo[f,h][1,5]dioxonin (TUNEPHOS), 1,2-bis(diphenylphosphino)propane (PROPHOS), 1,2-bis(phospholano)benzene (DuPHOS), 1,2-bis (phospholano)ethane (BPE), 1,2-bis(t-butylmethylphosphino)benzene (BenzP*), 1,2-bis[(2-methoxyphenyl) (phenylphosphino)]ethane (DIPAMP), 1,2-bis[2,5-dimethyl-3,4-dihydroxyphospholano]benzene (ROPHOS), 10,11,12,13-tetrahydrodiindeno[7,1-de:1',7'-fg][1,3,2]dioxaphosphocin-5-bis[1-phenylethyl]amine (SIPHOS-PE), 10,11,12,13-tetrahydrodiindeno[7,1-de:1',7'-fg][1,3,2]dioxaphosphocin-5-dimethylamine (SIPHOS), 10,11,12,13- tetrahydrodiindeno[7,1-de:1',7'-fg][1,3,2]dioxaphosphocin-5-phenoxy (ShiP), 2-(diphenylphosphino)-2'-methoxy-1,1'-binaphthyl (MOP), 2-(diphenylphosphinomethyl)-4-(dicyclohexylphosphino)-N-(t-butoxycarbonyl)pyrrolidine (BCPM), 2-(diphenylphosphinomethyl)-4-(dicyclohexylphosphino)-N-methyl-1-pyrrolidinecarboxamide (MCCPM), 2-(diphenylphosphinomethyl)-4-(diphenyl-phosphino)-N-(t-butoxycarbonyl)pyrrolidine (BPPM), 2-(diphenylphosphinomethyl)-4-(diphenylphosphino)pyrrolidine (PPM), 2-amino-1-phenylpropyldiphenylphosphine, 2,2'-bis(diphenylphosphino)-1,1'-biphenyl (DIPHEP), 2,2'-bis(N-diphenylphosphinoamino)-5,5',6,6',7,7',8,8'-octahydro-1,1'-binaphthyl (CTH-BINAM), 2,2'-bis[bis(3,5-dimethylphenyl)phosphino]-4,4',6,6'-tetramethoxybiphenyl (Xyl-Garphos) 2,3-bis(diphenylphosphino)-bicyclo[2.2.1]hept-5-ene (NORPHOS), 2,3-O-isopropylidene-2,3-dihydroxy-1,4-bis(diphenylphosphino)butane (DIOP), 2,4-bis(diphenylphosphino) pentane (BDPP), 4,12-bis(diphenylphosphino)-[2.2]-paracyclophane (PHANEPHOS), 4,4'-di-t-butyl-4,4',5,5'-tetrahydro-3,3'-bi-3H-dinaphtho[2,1-c:1',2'-e]phosphepin (BINAPINE), 4,5-bis(diphenylphosphinomethyl)-2,2-dimethyl-1,3-dioxolane (DIOP), 5,5'-bis[di(3,5-di-t-butyl-4-methoxyphenyl)phosphino]-4,4'-bi-1,3-benzodioxole (DTBM-STEGPHOS), 5,6,10,11,12,13-hexahydro-5-phenyl-4H-diindeno[7,1-cd:1,7-ef]phosphocin (SITCP), 6,6'-[(3,3'-di-t-butyl-5,5'-dimethoxy-1,1'-biphenyl-2,2'-diyl)bis(oxy)]bis(dibenzo[d,f][1,3,2]dioxaphosphepin) (DIPHEPHOS), 6,6'-{[1,3-dimethyl-1,3-propanediyl]bis(oxy)}bis[4,8-bis(t-butyl)-2,10-dimethoxy-bibenzo[d,f][1,3,2]dioxaphosphepin] (Chiraphite), 7,7'-bis(diphenylphosphino)-2,2',3,3'-tetrahydro-1,1'-spirobiindane (SDP), bis-(1,2-diphenylphosphino)propane (PROPHOS), bis(diphenyl-phosphino)butane (CHIRAPHOS), bis(diphenylphosphino)dicyclopentane (BICP), bis(diphenylphospino)-1,1'-binaphthyl (BINAP), N-[dinaphtho[2,1-d:1',2'-f][1,3,2]dioxaphosphepin-4-yl]-1,1,1-neomenthyldiphenylphosphine (NMDPP), and trifluoromethanesulfonamide (METAMORPhos).

Chiral nitrogen-containing ligands include, but are not limited to, α,α-diphenyl-2-pyrrolidinemethanol (DPP), and α,α-diphenyl-2-pyrrolidinemethanol trimethylsilyl ether (DPPT), 1,1-bis(4-methoxyphenyl)-3-methyl-1,2-butanediamine (DAIPEN), 1,2-bis(2-hydroxyphenyl)ethylenediamine (DPEN), 1,2-bis(4-cyanophenyl)ethylenediamine, 1,2-bis(4-dimethylaminophenyl) ethylenediamine, 1,2-bis(4-dimethylaminophenyl) ethylenediamine, 1,2-bis(4-nitrophenyl)ethylenediamine, 1,2-cyclohexanediamino-N,N'-bis(3,5-di-t-butylsalicylidene) (Jacobsen Ligand), 1,2-diaminocyclohexane (DACH), 1,2-diphenylethylenediamine, 2-(4-t-butyl-4,5-dihydro-oxazol-2-yl)propan-2-ol, 2-(methanamine)-1H-benzimidazole (BIMAH), 2,2'-bipyrrolidine, 2,2'-diamino-1,1'-binaphthyl, 2,3-bis(tert-butylmethylphosphino)quinoxaline, 2,6-bis[(3a,8a-dihydro-8H-indeno[1,2-d]oxazolin-2-yl]pyridine (Indenyl-PYBOX), 2,6-bis[(-4-(i-propyl)-2-oxazolin-2-yl]pyridine (i-Pr-PYBOX), 7,7-bis[(phenyl)oxazol-2-yl)]-2,2,3,3-tetrahydro-1,1-spirobiindane (SpiroBOX), chichonidine, cis-1-aminoindan-2-ol, dihydroquinidine (DHQD), dihydroquinine (DHQ), N,N'-1,2-diaminocyclohexanediylbis(2-pyridinecarboxamide), N,N'-bis(2-pyridylmethyl)-2,2'-bipyrrolidine (PDP), N,N'-1,2-diaminocyclohexanediylbis(2-pyridinecarboxamide) (DACH-pyridyl), quinine and sparteine.

Chiral dienes may include monocyclic dienes and bicyclic dienes. An example of a monocyclic diene is diphenylcyclooctadiene (Ph-cod*). Bicyclic dienes based on a bicyclo [2.2.1]hepta-2,5-diene skeleton (nbd*) include, but are not limited to, 2,5-dibenzylbicyclo[2.2.1]hepta-2,5-diene (Bn-nbd*), 2,5-dimethylbicyclo[2.2.1]hepta-2,5-diene (Me-nbd*), 2,5-diphenylbicyclo[2.2.1]hepta-2,5-diene (Ph-nbd*), and 2,5-bis(2,4,6-trimethylbenzyl)-bicyclo[2.2.1]hepta-2,5-diene (Bn-nbd*) (Mm-nbd*). Bicyclic dienes based on a bicyclo[2.2.2]octa-2,5-diene skeleton (bod*) include, but are not limited to, 2,5-diphenylbicyclo[2.2.2]octa-2,5-diene (Ph-bod*), 2,5-diphenylbicyclo[2.2.2]octa-2,5-diene (Ph-bod*) and 2,5-dibenzylbicyclo[2.2.2]octa-2,5-diene (Bn-bod*). Bicyclic dienes based on a bicyclo[3.3.1]nona-2,6-diene skeleton (bnd*) include, but are not limited to, 2,6-diphenylbicyclo[3.3.1]nona-2,6-diene (Ph-bnd*) and 2,6-ditolylbicyclo[3.3.1]nona-2,6-diene (Tol-bnd*). Bicyclic dienes based on a bicyclo[3.3.2]deca-2,6-diene (bdd*) skeleton include, for example, 2,6-diphenylbicyclo[3.3.2]deca-2,6-diene (Ph-bdd*). Other chiral ligands may be identified, for example, in Aldrichimica Acta, Vol. 42, No. 2 (2009), which is hereby incorporated by reference with respect to the listing of ligands. In an exemplary embodiment, the chiral ligand may be 2,5-diphenylbicyclo[2.2.2]octa-2,5-diene (Ph-bod*). The 2,5-diphenylbicyclo[2.2.2]octa-2,5-diene (Ph-bod*) may be chosen from (1S,4R)-2,5-diphenylbicyclo[2.2.2]octa-2,5-diene; (1S,4S)-2,5-diphenylbicyclo[2.2.2]octa-2,5-diene; (1R,4S)-2,5-diphenylbicyclo[2.2.2]octa-2,5-diene; and (1R,4R)-2,5-diphenylbicyclo[2.2.2]octa-2,5-diene.

Any chiral ligands mentioned above may be derivatized, for example, with one or more alkyl groups, such as methyl or ethyl, or one or more aryl groups, such as phenyl, benzyl, tolyl, or methoxyphenyl. Other examples of chiral phosphine, nitrogen-containing and diene ligands may be found in Catalytic Asymmetric Synthesis, Second Edition, edited by I. Ojima, Wiley-VCH, Inc. (2000); M. McCarthy and P. J. Guiry, "Axially chiral bidentate ligands in asymmetric catalysis," Tetrahedron, 57:3809-3844 (2001); and W. Tang and Z. Zhang, "New Chiral Phosphorous Ligands for Enantioselective Hydrogenation," Chemical Reviews, 103: 3029-3069 (2003). In addition to the above-mentioned dienes that possess an intrinsic stable chirality, some achiral dienes may also exhibit chirality upon coordination to a transition metal.

The weight ratio of the transition metal catalyst to the chiral ligand can and will vary. In general, the weight ratio of the transition metal catalyst to the chiral ligand will range from about 1:0.1 to about 1:10. In certain embodiments, the weight ratio of the transition metal catalyst to the chiral ligand may range from about 1:0.1 to about 1:0.3, from about 1:0.3 to about 1:1, from about 1:1 to about 1:3, or from about 1:3 to about 1:10. In an exemplary embodiment, the weight ratio of the transition metal catalyst to the chiral ligand may be about 1:1.5.

(v) Optional Proton Acceptor

The reaction mixture, as detailed herein, may also comprise a proton acceptor. The proton acceptor will vary depending on the starting substrates, the transition metal, and the chiral ligand. Non-limiting examples of proton acceptors include sodium hydroxide, potassium hydroxide, calcium hydroxide, barium hydroxide, cesium carbonate, sodium bicarbonate, potassium bicarbonate, sodium carbonate, potassium carbonate, sodium borate, sodium dihydrogen phosphate, disodium hydrogen phosphate, sodium methoxide, sodium tert-butoxide, and potassium tert-butoxide.

The molar ratio of the compound of Formula (I) to the proton acceptor may vary depending, for example, on the substrate being used, the nature of the catalyst, and the solvent of the process. In general, the molar ratio of the compound of Formula (I) and the proton acceptor will range from about 1:0.01 to about 1:2.0. In certain embodiments, the molar ratio of the compound of Formula (I) to the proton acceptor may range from about 1:0.01 to about 1:0.05, from about 1:0.05 to about 1:0.1, from about 1:0.1 to about 1:0.50, from about 1:0.50 to about 1:1.0, or from 1:1.0 to 1:2.0. In one exemplary embodiment, the molar ratio of the compound of Formula (I) to the proton acceptor may range from about 1:0.2 to about 1:1.0.

(vi) Optional Amine

In some embodiments, the reaction mixture may further comprise an amine. Depending on the starting substrates, the transition metal catalyst, and the chiral ligand, and amine may be a secondary amine, a tertiary amine, or combinations thereof. The amine may be chiral or achiral. Non-limiting examples of suitable secondary amines include ethyl methyl amine, dimethyl amine, diethyl amine, dicyclohexyl amine, methyl cyclohexyl amine, phenyl ethyl amine, dibenzyl amine, methyl benzyl amine, ethyl benzyl amine, cyclohexyl phenyl amine, dibutyl amine, ditertiarybutyl amine, dipropyl amine, dipentylamine, dicyclohexyl amine, piperidine, 2-methylpiperidine, 2,5-di methylpiperidine, 2,6-di methylpiperidine, piperazine, 2-methylpiperazine, 2,6-dimethylpiperazine, and morpholine. Non-limiting examples of suitable tertiary amines include trimethylamine, triethylamine, diisopropylethylamine, tripropylamine, tributylamine, 4-methylmorpholine, 4-ethylmorpholine, N-methylpyrrolidine, N-methylpiperidine, 1,8-diazabicyclo[5.4.0]undec-7-ene, pyrazine, 4-dimethylaminopyridine, and pyridine. Non-limiting examples of chiral secondary amines (R)-α-methylbenzylamine, (S)-α-methylbenzylamine, α,α-diphenyl-2-pyrrolidinemethanol (DPP), and α,α-diphenyl-2-pyrrolidinemethanol trimethylsilyl ether (DPPT).

The molar ratio of the compound of Formula (I) to the amine may vary depending, for example, on the substrate being used, the nature of the catalyst, and the solvent of the process. In general, the molar ratio of the compound of Formula (I) and the amine will range from about 1:0.01 to about 1:1.0. In certain embodiments, the molar ratio of the compound of Formula (I) to the amine may range from about 1:0.01 to about 1:0.025, from about 1:0.025 to about 1:0.05, from about 1:0.05 to about 1:0.10, from about 1:0.10 to about 1:0.5, or from 1:0.5 to 1:1.0. In one exemplary embodiment, the molar ratio of the compound of Formula (I) to the amine may range from about 1:0.05 to about 1:0.5. In another exemplary embodiment, the molar ratio of the comprising Formula (I) to the amine may range from about 1:0.1 to about 1:0.5. In a further exemplary embodiment, the molar ratio of the compound of Formula (I) to the amine may be about 1:0.4.

(vii) Solvent

The reaction mixture, as detailed herein, may also comprise a solvent. The solvent can and will vary depending on the starting substrates, the transition metal catalyst, and the chiral ligand used in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In one exemplary embodiment, the solvent may be a combination of polar solvents. For example, the solvent may be a combination of tetrahydrofuran, water, and an alcohol, such as methanol. The combination of methanol/THF may be in any volume to volume ratio, ranging from 99:1 to 1:99, for example, including, 75:25, 50:50, 25:75, and at values between the listed values. An amount of water may be incorporated in any volume to volume ratio. In one embodiment, the combination of methanol/THF/water is about 71:17:12.

In general, the volume to weight ratio of the solvent to the compound of Formula (I) will range from about 0.5:1 to about 50:1. In various embodiments, the volume to weight ratio of the solvent to the compound of Formula (I) may range from about 0.5:1 to about 2:1, from about 2:1 to about 5:1, from about 5:1 to about 25:1, or from about 25:1 to about 50:1. In an exemplary embodiment, the volume to weight ratio of the solvent to the compound of Formula (I) may range from about 5:1 to about 20:1.

The pH of the reaction mixture may be adjusted to optimize activity of the transition metal catalyst. In general, the optimal pH will vary depending upon the nature of the transition metal catalyst. A person of skill in the art will know how to determine the optimal pH level for the transition metal catalyst of interest.

(viii) Reaction Conditions

In general, the reaction of step A will be conducted at a temperature that ranges from about −10° C. to about 80° C. In various embodiments, the temperature of the reaction may range from about −10° C. to about 0° C., 0° C. to about 10° C., 10° C. to about 20° C., from about 20° C. to about 30° C., from abut 30° C. to about 40° C., from about 40° C. to about 60° C., or from about 60° C. to about 803. In one embodiment, the reaction may be conducted at temperature that ranges from about 10° C. to about 40° C., or from about 20° C. to about 30° C. In another embodiment, the temperature of the reaction may be about room temperature (~23° C.). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as chromatography (e.g., HPLC). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an exemplary embodiment, the reaction may be allowed to proceed for about 0.5 hour to about 2 hours. In this context, a "completed reaction" generally means that the reaction mixture contains a significantly diminished amount of the compound of Formula (I). Typically, the amount of the compound of Formula (I) remaining in the reaction mixture at the end of the reaction may be less than about 10%, less than about 5%, or less than about 2%.

The compound of Formula (II) may have a yield of at least about 50%. In various embodiments, the compound of Formula (II) may have a yield of at least about 50%, at least about 60%, at least about 65%, at least about 70%, at least about 75%, at least about 80%, at least about 85%, at least about 90%, at least about 95%, or at least about 99%.

The compound of Formula (II) may be produced with a percent enantiomeric excess (EE %) at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, at least about 99%, at least about 99.5%, or at least about 99.9%. The compound of Formula (II) produced may be R or S stereochemistry, in specific embodiments, the compound of Formula (II) produced may be R stereochemistry.

(b) Step B of the 5-Step Process

Step B results in the addition of a methylene substituent alpha to the carbonyl of the compound of Formula (II) to result in the compound of Formula (III). A number of reagents are suitable to accomplish the transformation of Step B. In one embodiment, Step B involves contacting the compound of Formula (II) with a methylenyl addition agent such as a methyleneimminium halide or a formaldehyde reagent.

(i) Methylenyl Addition Agent

Two different methylenyl addition agents may be utilized in forming a α-alkene group next to the carbonyl group, methyleneimminium halide reagent and a formaldehyde reagent.

Methyleneimminium Halide.

In one embodiment, the methylenyl addition agent may be a methyleneimminium halide, for example an N,N-dialkyl-methyleneimmium halide. The halide may be selected from fluoride, chloride, bromide or iodide. In an exemplary embodiment, the methylenyl addition agent may be N,N-dimethylmethyleneimminium chloride.

The molar ratio of the compound of Formula (II) to the methyleneimminium halide may range from about 1:0.5 to about 1:15. In certain embodiments, the molar ratio of the compound of Formula (II) to the methyleneimminium halide may range from about 1:0.5 to about 1:1, from about 1:1 to about 1:2, from about 1:2 to about 1:4, from about 1:4 to about 1:8, or from about 1:8 to about 1:15. In one embodiment, the molar ratio of the compound of Formula (II) to the methyleneimminium halide may range from about 1:1 to about 1:5, or from about 1:2 to about 1:3. In another embodiment, the molar ratio of the compound of Formula (II) to the methyleneimminium halide may be about 1:2.5.

Formaldehyde Reagent.

In another embodiment, the methylenyl addition agent may be a formaldehyde reagent. In some embodiments, the formaldehyde reagent is a paraformaldehyde, which may be added to the reaction mixture or prepared in situ. In one embodiment, the formaldehyde reagent is an aqueous solution of formaldehyde ranging from about 20% to about 60% formaldehyde in water. In one embodiment, the formaldehyde reagent is an aqueous solution of formaldehyde ranging from about 35% to about 45% formaldehyde in water.

Generally, the formaldehyde reagent is contacted with the compound of Formula (II) in the presence of a catalyst. The catalyst may be, without limitation, monocarboxylic acids and secondary amines. More particularly the catalyst may be proline, imidazolidinone or derivatives thereof, such as, by way of non-limiting example, methyl prolinate, 4-benzyl-2-(tert-butyl)-1-methylimidazolidine, prolylserine, prolylglycine, and N-propylpyrrolidine-2-carboxamide. In another embodiment, the catalyst may be an ammonium salt, such as, for example a salt of N-methylalanine, quinolone, piperidine, morpholine, pyrrolidine, or diisopropyl amine. Suitable salts are known in the art, for example, trifluoroacetic acid, acetic acid, or hydrochloric acid salts.

The molar ratio of the compound of Formula (II) to the formaldehyde reagent may range from about 1:0.5 to about 1:15. In certain embodiments, the molar ratio of the compound of Formula (II) to the formaldehyde reagent may range from about 1:0.5 to about 1:1, from about 1:1 to about 1:2, from about 1:2 to about 1:4, from about 1:4 to about 1:8, or from about 1:8 to about 1:15. In an exemplary embodiment, the molar ratio of the compound of Formula (II) to the formaldehyde reagent may range from about 1:1 to about 1:5, or from about 1:2 to about 1:3. In another exemplary embodiment, the molar ratio of the compound of Formula (II) to the formaldehyde reagent may be about 1:1.

(ii) Solvent

The reaction mixture generally also comprises a solvent. Suitable solvents include polar protic solvents, polar aprotic solvents, non-polar solvents, and combinations thereof, examples of which are described above in section (I)(a)(vii). In an exemplary embodiment, the solvent may be a combination of polar aprotic solvents. For example, the reaction may be conducted in the presence of a combination of dichloromethane and an organic base. The organic base may be selected from, without limitation, triethylamine, N,N-diisopropylethylamine, N-methylmorphine, N-methylpiperidine, and the like.

In general, the volume to weight ratio of the solvent to the compound of Formula (II) may range from about 1:1 to about 100:1. In various embodiments, the volume to weight ratio of the solvent to the compound of Formula (II) may range from about 1:1 to about 5:1, from about 5:1 to about 25:1, from about 25:1 to about 75:1, or from about 75:1 to about 100:1. In an exemplary embodiment, the volume to weight ratio of the solvent to the compound of Formula (II) may range from about 25:1 to about 75:1.

(iii) Reaction Conditions

The reaction using the methylenyl addition agent may be conducted at a temperature that ranges from about 0° C. to about 83° C. In various embodiments, the temperature of the reaction may range from about 0° C. to about 20° C., from about 20° C. to about 30° C., from about 30° C. to about 40° C., from about 40° C. to about 60° C., or from about 60° C. to about 80° C. In exemplary embodiments the reaction may be conducted at temperature that ranges from about 10° C. to about 40° C., or from about 20° C. to about 30° C. In one exemplary embodiment, the temperature of the reaction may be about room temperature. The reaction generally will be conducted under inert atmosphere, for example under nitrogen, argon or helium.

The reaction using the formaldehyde agent may be conducted at a temperature that ranges from about 0° C. to about 80° C. In various embodiments, the temperature of the reaction may range from about 0° C. to about 20° C., from about 20° C. to about 30° C., from about 30° C. to about 40° C., from about 40° C. to about 60° C., or from about 60° C. to about 80° C. In exemplary embodiments the reaction may be conducted at temperature that ranges from about 10° C. to about 40° C., or from about 20° C. to about 30° C. In one exemplary embodiment, the temperature of the reaction may be about 45° C. Other conditions for the formaldehyde reaction may be found, for example, in Pihko et al., "Mild Organocatalytic α-Methylenation of Aldehydes," J. Org. Chem. 2006, 71, 2538-2541 (2006) or Bugarin et al., "Efficient, Direct α-Methylenation of Carbonyls Mediated by Diisopropylammonium Trifluoroacetate," Chem. Comm. 2010, 46, 1715-1717, each of which are hereby incorporated by reference.

Generally, the reaction is allowed to proceed for a sufficient period of time until the reaction is complete, as determined by any method known to one skilled in the art. The reaction may be allowed to proceed for a time that ranges from about 4 hours to about 30 hours. In some embodiments, the duration of the reaction may range from about 4 hours to about 10 hours, from about 10 hours to about 18 hours, or from about 18 hours to about 30 hours. In one exemplary embodiment, the reaction may be allowed to proceed overnight. The amount of the compound of Formula (II) remaining in the reaction mixture at the end of the reaction may be less than about 10%, less than about 5%, or less than about 2%.

The compound of Formula (III) may have a yield of at least about 50%. In certain embodiments, the yields of the compound of Formula (III) may be at least about 50%, at least about 60%, at least about 65%, at least about 70%, at least about 75%, at least about 80%, at least about 85%, at least about 90%, at least about 95%, or at least about 99%.

(c) Step C of the 5-Step Process

Step C comprises contacting the compound of Formula (III) with a hydrogen source to form a compound of Formula (IV). The hydrogen source may be chosen from, by way of non-limiting example, gas comprising molecular hydrogen, silicon hydride, formic acid, or diimide.

(i) Catalytic Hydrogenation with Molecular Hydrogen

In one embodiment, Step C of the process involves catalytic hydrogenation in the presence of molecular hydrogen ($H_2$). A gas comprising molecular hydrogen may be contacted with the reaction mixture by shaking, vigorous stirring, or sparging. Typically, molecular hydrogen is added to the headspace of the reaction vessel. Molecular hydrogen may be used singly or in combination with inert atmospheric gases, such as nitrogen, argon or helium. Molecular hydrogen may be used at a pressure of about 10 to about 100 psi. In some embodiments, the pressure may be about 10 to about 20 psi, about 20 to about 30 psi, about 30 to about 40 psi, about 40 to about 50 psi, about 50 to about 60 psi, about 70 to about 80 psi, about 80 to about 90 psi, or about 90 to about 100 psi. In an exemplary embodiment, the molecular hydrogen may be present at a pressure of about 50 psi. Preferably, a gas containing greater than about 90, 95, or 99.5% hydrogen by volume is used. The gas may be mixed with an inert gas, or, in some instances with air.

The hydrogenation of step C generally is conducted in the presence of a catalyst. Representative catalysts for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. Further examples of transition metal catalysis and variations thereof can be found about at section (I)(a)(i). In some embodiments, an inert substrate may be used, such as carbon, activated charcoal, alumina, barium sulfate, calcium carbonate or polystyrene. In other embodiments, the catalyst may be finely powdered or highly porous to provide a greater surface area of contact between the catalyst and the compound of Formula (III). In exemplary embodiments, the catalyst may be chosen from palladium, platinum, nickel, cobalt, and iron. In one exemplary embodiment, the catalyst may be palladium on carbon.

The molar ratio of the compound of Formula (III) to the catalyst may range from about 1:0.001 to 1:0.1. In various embodiments, the molar ratio of the compound of Formula (III) to the catalyst may range from about 1:0.001 to about 1:0.003, from about 1:0.003 to about 1:0.01, from about 1:0.01 to about 1:0.03, or from about 1:0.03 to about 1:0.1. In exemplary embodiments, the molar ratio of the compound of Formula (III) to the catalyst may range from about 1:0.005 to about 1:0.02.

(ii) Alternative Hydrogen Sources

Other reactions and reagents may be suitable to convert the compound of Formula (III) to the compound of Formula (IV). Other suitable hydrogen sources include diimide, formic acid in the presence of triethylamine, and silicon hydride. Such reactions are described in the art. These reactions may be catalytic and include a catalyst as described in section (I)(a)(i) or a catalyst known in the art. In one embodiment, the hydrogen source is a diimide. Conditions for a diimide reaction may be as described in Smit et al., "Reduction of Carbon-Carbon Double Bonds Using Organocatalytically Generated Diimide," J. Org. Chem., 2008, 73, 9482-9485, which is hereby incorporated by reference.

(iii) Solvent

Step C may be conducted in the presence of a solvent chosen from a polar protic solvent, a polar aprotic solvent, a non-polar solvent, and combinations thereof. A suitable solvent may a solvent as defined above in section (I)(a)(vii). In an exemplary embodiment, the solvent may be ethyl acetate.

The volume to weight ratio of the solvent to the compound of Formula (III) may range from about 2:1 to about 200:1. In certain embodiments, the volume to weight ratio of the solvent to the compound of Formula (III) may range from about 2:1 to about 10:1, from about 10:1 to about 30:1, from about 30:1 to about 100:1, or from about 100:1 to about 200:1. In one exemplary embodiment, volume to weight ratio of the solvent to the compound of Formula (III) may range from about 50:1 to about 200:1.

(iv) Reaction Conditions

In general, the reaction of step C may be conducted at a temperature from about 10° C. to about 60° C. In various embodiments, the temperature of the reaction may range from about 10° C. to about 20° C., from about 20° C. to about 30° C., from about 30° C. to about 40° C., from about 40° C. to bout 50° C., or from about 50° C. to about 60° C. In exemplary embodiments, the reaction may be conducted at temperature that ranges from about 10° C. to about 40° C. or from bout 20° C. to about 30° C. In one exemplary embodiment, the temperature of the reaction may be about room temperature.

The reaction may be allowed to proceed for a time that ranges from about 30 minutes to about 10 hours. In various embodiments, the duration of the reaction may range from about 0.5 hour to about 2 hours, from about 2 hours to about 4 hours, or from about 4 hours to about 10 hours. In one exemplary embodiment, the reaction may proceed for about 2 hours to about 4 hours. The amount of the compound of Formula (III) remaining in the reaction mixture at the end of the reaction may be less than about 10%, less than about 5%, or less than about 2%.

In general, the compound of Formula (IV) may have a yield of at least about 50%. In certain embodiments, the compound of Formula (IV) may have a yield of at least about 50%, at least about 55%, at least about 60%, at least about 65%, at least about 70%, at least about 75%, at least about 80%, at least about 85%, at least about 90%, at least about 95%, or at least about 99%.

In embodiments, the compound of Formula (IV) contains two chiral carbons and the compound of Formula (IV) may be produced with an diastereomeric excess of at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, at least about 99%, at least about 99.5%, or at least about 99.9%. For the compound of Formula (IV) where $R^1$ is hydrogen, the desired diastereomer produced is (2R,3R)-(3-methoxyphenyl)-2-pentanal.

(d) Step D of the 5-Step Process

Step D comprises contacting the compound of Formula (IV) with a secondary amine comprising Formula (X) to form a compound of Formula (V). In one embodiment, Step D of the process comprises contacting a compound of Formula (IV) with a secondary amine comprising Formula (X) under conditions for reductive amination to form a compound of Formula (V). Generally, reductive amination requires an amine agent and a reducing agent.

(i) Secondary Amine of Formula (X)

The secondary amine comprising Formula (X) is a compound of formula $NR^{10}R^{11}$, wherein $R^{10}$ and $R^{11}$ are as defined above, namely, they are independently chosen from hydrocarbyl and substituted hydrocarbyl. For example, $R^{10}$ and $R^{11}$ may be alkyl, substituted alkyl, aryl, or substituted aryl. In some embodiments, $R^{10}$ and $R^{11}$ together may form a ring or ring system selected from the group consisting of carbocyclic, heterocyclic, aryl, heteroaryl, and combinations thereof. Examples of suitable secondary amines include aliphatic secondary amines, aromatic secondary amines, and aliphatic-aromatic secondary amines. Non-limiting examples of suitable secondary amines include ethyl methyl amine, dimethyl amine, diethyl amine, dicyclohexyl amine, methyl cyclohexyl amine, ethyl phenyl amine, dibenzyl amine, methyl benzyl amine, ethyl benzyl amine, cyclohexyl phenyl amine, dibutyl amine, and ditertiarybutyl amine. In some embodiments, $R^{10}$ and $R^{11}$ may together form a ring, for example forming pyrrolidine or piperidine. In an exemplary embodiment, the secondary amine may be dimethylamine.

In general, the molar ratio of the compound of Formula (IV) to the secondary amine of Formula (X) may range from about 1:0.5 to about 1:60. In various embodiments, the molar ratio of the compound of Formula (IV) to the secondary amine comprising Formula (X) may range from about 1:0.5 to about 1:10, from about 1:10 to about 1:15, from about 1:15 to about 1:30, or from about 1:30 to about 1:60. In exemplary embodiments, the molar ratio of the compound of Formula (IV) to the secondary amine comprising Formula (X) may range from about 1:0.5 to about 1:5.

(ii) Reducing Agent

Step D may be conducted in the presence of a reducing agent. Examples of suitable reducing agents include, but are not limited to, hydrides (e.g., hydrogen iodide, hydrogen sulfide, lithium aluminum hydride, sodium borohydride, sodium cyanoborohydride, sodium triacetoxyborohydride, silicon hydride, and the like), or combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like), samarium iodide, Hantzsch ester, and others. Other reagents such as transition metal catalysts in the presence of molecular hydrogen may also facilitate the reaction. These catalysts using molecular hydrogen are described in section (I)(c)(i). In one exemplary embodiment, the reducing agent present during step D may be sodium cyanoborohydride.

The weight ratio of the compound of Formula (IV) to the reducing agent may range from about 1:0.3 to about 1:5. In some embodiments, the weight ratio of the compound of Formula (IV) to the reducing agent may range from about 1:0.3 to about 1:0.6, from about 1:0.6 to about 1:0.8, from about 1:0.8 to about 1:1, from about 1:1 to about 1:1.2, from about 1:1.2 to about 1:1.4, from about 1:1.4 to about 1:1.6, from about 1:1.6 to about 1:1.8, or from about 1:1.8 to about 1:2. In one exemplary embodiment, the molar ratio of the compound of Formula (IV) to the reducing agent may range from about 1:0.8 to about 1:1.

(iii) Solvent

Step D may be conducted in the presence of a solvent chosen from a polar protic solvent, a polar aprotic solvent, a non-polar solvent, and combinations thereof. Suitable solvents are described above in section (I)(a)(vii). In an exemplary embodiment, the solvent may be N,N-dimethylformamide.

The volume to weight ratio of the solvent to the compound of Formula (IV) may range from about 1:1 to about 100:1. In various embodiments, the volume to weight ratio of the solvent to the compound of Formula (IV) may range from about 1:1 to about 5:1, from about 5:1 to about 25:1, from about 25:1 to about 75:1, or from about 75:1 to about 100:1. In an exemplary embodiment, the volume to weight ratio of the solvent to the weight of compound of Formula (IV) may range from about 20:1 to about 50:1.

(iv) Reaction Conditions

Step D may be conducted at a temperature that ranges from about 0° C. to about 80° C. In certain embodiments, the temperature of the reaction may range from about 0° C. to about 20° C., from about 20° C. to about 0° C., from about 30° C. to about 40° C., from about 40° C. to about 60° C., or from about 60° C. to about 80° C. In exemplary embodiments, the reaction may be conducted at temperature that ranges from about 10° C. to about 40° C., or from about 20° C. to about 30° C. In one exemplary embodiment, the temperature of the reaction may be about room temperature.

Step D may also be conducted under inert atmosphere, for example under nitrogen, argon or helium.

The duration of the reaction may range from about 5 minutes to about 10 hours. In some embodiments, the duration of the reaction may range from about 5 minutes to about 30 minutes, from about 30 minutes to about 2 hours, from about 2 hours to about 4 hours, or from about 4 hours to about 10 hours. In an exemplary embodiment, the reaction may be allowed to proceed for about 0.5 hour to about 2 hours. The amount of the compound of Formula (IV) remaining in the reaction mixture at the end of the reaction may be less than about 10%, less than about 5%, or less than about 2%.

The compound of Formula (V) may have a yield of at least about 50%. In some embodiments the compound of Formula (V) has a yield of at least about 50%, at least about 60%, at least about 70%, at least about 75%, at least about 80%, at least about 85%, at least about 90%, at least about 95%, or at least about 99%.

(v) Other Reagents for Reductive Amination

A number of reagents and conditions for reductive amination are known in the art and may be suitable for the transformation from the compound of Formula (IV) to the compound of Formula (V). Examples from the literature of additional suitable reagents and conditions for reductive amination include Gomez et al., "The Reductive Amination of Aldehydes and Ketones and the Hydrogenation of Nitriles: Mechanistic Aspects of Selectivity and Control," Adv. Synth. Catal. 2002, 334, No. 10, 1037-1057; Tiwari et al., "Recent Development on Catalytic Reductive Amination and Applications," Current Organic Chem. 12, 1093-1115 (2008); Apodaca et al., "Direct Reductive Amination of Aldehydes and Ketones Using Phenylsilane: Catalysis by Dibutyltin Dichloride." Organic Lett., 2001, Vol. 3, No. 11, 1745-1448; and Williams et al., "A One-Pot Process for the Enantioselective Synthesis of Amines via Reductive Amination under Transfer Hydrogenation Conditions," Org. Letters, 2003, Vol. 5, No. 22, 4227-4230; each of which are incorporated by reference.

(e) Step E of the 5-Step Process

Step E comprises contacting the compound of Formula (V) with an O-dealkylating reagent to form the compound of Formula (VI). In an exemplary embodiment, the reagent is an O-demethylation reagent. 0-demethylation is described, for example, in "Protective Groups in Organic Synthesis" by T. W. Greene, John Wiley & Sons, 2006.

(i) O-Dealkylating Agent

A variety of O-dealkylating agents may be used in the reaction of step E. Examples of suitable O-dealkylating agents include, but are not limited to, nitrogen bases, such as ammonia, propylamine, diethylamine, trimethylamine, hexyldimethylamine, hydroxyethylamine, benzylamine, tetramethylethylenediamine, N-methylpyrrolidine, triethylenediamine and hexamethylenetetramine; formic esters, such as 1-chloroethyl chloroformate, ethyl chloroformate and tert-butyl chloroformate; thiolate O-dealkylating agents such as sodium sulfide, sodium hydrogen sulfide, tetraalkylammonium sulfide, sodium methanethiolate, potassium ethanethiolate, sodium 2-propanethiolate, sodium xylenethiolate, potassium ethylxanthate, ammonium dimethyl dithiophosphate, potassium diethyl dithiophosphate, tetramethylammonium diisopropyl dithiophosphate, trimethylbenzylammonium sulfide, methionine, and trimethylammonium di methyl thiophosphate; hydrogen halides such as hydroiodic acid, hydrobromic acid, or hydrochloric acid; inorganic salts, such as lithium chloride, sodium iodide and calcium chloride; boron tribromide, methanesulfonic acid, trifluoromethane sulfonic acid, pyridine hydrochloride, and certain enzymes. In exemplary embodiments, the O-dealkylating agent may be a hydrogen halide or a sulfonic acid. An exemplary hydrogen halide is aqueous hydrobromic acid.

The weight ratio of the O-dealkylating agent to the compound of Formula (V) generally will range from about 1:1 to about 400:1. In some embodiments, the weight ratio of the O-dealkylating agent to the compound of Formula (V) may range from 1:1 to about 10:1, from about 10:1 to about 100:1, from about 100:1 to about 200:1, or from about 200:1 to about 400:1. In an exemplary embodiment, weight ratio of the O-dealkylating agent to the compound of Formula (V) may range from about 200:1 to about 250:1.

(ii) Reaction Solvent.

The reaction mixture may optionally comprise a solvent in addition to the 0-dealkylating agent. Suitable solvents are described above in section (I)(a)(vii). In an exemplary embodiment, no additional solvent was added to the reaction mixture; in other words, the O-dealkylating agent acts as a solvent in the reaction.

(iii) Reaction Conditions.

Typically, step E is conducted at a temperature that ranges from about 50° C. to about 200° C. In certain embodiments the temperature of the reaction may range from about 50° C. to about 80° C., from about 80° C. to about 100° C., from about 100° C. to about 120° C., from about 120° C. to about 150° C., or from about 150° C. to about 200° C. In exemplary embodiments, the reaction is conducted at a temperature that ranges from about 80° C. to about 150° C., or from about 100° C. to about 120° C. Step E may also be conducted under an inert atmosphere, for example under nitrogen, argon or helium.

The reaction of step E may be allowed to proceed for about 10 minutes to about 12 hours. In some embodiments, the duration of the reaction may range from about 10 minutes to about 1 hour, from about 1 hour to about 2 hours, from about 2 hours to about 4 hours, or from about 4 hours to about 12 hours. In an exemplary embodiment, the reaction may be allowed to proceed for about 1 hour to about 3 hours. The amount of the compound of Formula (V) remaining in the reaction mixture at the end of the reaction may be less than about 10%, less than about 5%, or less than about 2%.

The compound of Formula (VI) may have a yield of at least about 50%. In some embodiments, the yield of the compound of Formula (VI) may be at least about 50%, at least about 60%, at least about 65%, at least about 70%, at least about 75%, at least about 80%, at least about 85%, at least about 90%, at least about 95%, or at least about 99%.

In embodiments, the compound of Formula (VI) contains two chiral centers and the compound of Formula (VI) may be produced with an diastereomeric excess of at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, at least about 99%, at least about 99.5%, or at least about 99.9%. The compound of Formula (VI), the desired diastereomer produced is (2R,3R)-(3-hydroxyphenyl)-N,N-triemethylpentan-1-amine.

(f) Exemplary Embodiments

In exemplary embodiments, R may be methyl; each of $R^3$, $R^4$, $R^5$, and $R^7$ may be hydrogen; $R^1$ may be hydrogen; $R^2$ may be ethyl; and both $R^{10}$ and $R^{11}$ may be methyl. The compound of Formula (I) may be m-methoxyphenylboronic acid, 3-methoxyphenyl trifluoroborate, 3-methoxyphenylboronic acid pinacol ester, 3-methoxyphenylboronic ester, or a compound derived from 3-methoxyphenylboroxine. In Step A, the transition metal catalyst may be [RhCl(C$_2$H$_4$)$_2$]$_2$, the chiral ligand may be (1S,4S)-2,5-diphenylbicyclo[2.2.2]octa-2,5-diene, the proton acceptor may be potassium hydroxide, and the amine may be 4-methylmorpholine. In Step B, the methylenyl addition agent may be N,N-dimethylmethyleneimminium chloride. In step C, the hydrogen source may be molecular hydrogen and the hydrogenation catalyst may be 5% Pd on carbon with a molecular hydrogen pressure of 50 psi. In step D, the secondary amine may be dimethylamine and the reducing agent may be sodium cyanoborohydride. In step E, the O-dealkylating agent may be 48% aqueous hydrobromic acid reacted at 110° C. without additiond solvent.

In some exemplary embodiments, the molar ratio of the compound of Formula (I) to the transition metal catalyst may be about 1:0.015; the weight ratio of the transition metal catalyst to the chiral ligand may be about 1:1.5; step A may be conducted in the presence of tetrahydrofuran and methanol and water at a temperature of about 23° C. under nitrogen; and the compound of Formula (II) has a yield of at least about 50% and an enantiomeric excess of at least about 50%. The molar ratio of the compound of Formula (II) to the methylenyl addition agent may be about 1:2.4; and step B may be conducted in the presence of dichloromethane and triethylamine and at a temperature of about 23° C. under nitrogen. The reaction of step C may be conducted with molecular hydrogen in the presence of palladium on carbon as a catalyst; and step C may be conducted in the presence of ethyl acetate and at a temperature of about 23° C. The molar ratio of the secondary amine comprising Formula (X) to the compound of Formula (IV) may be about 3.2:1; the reaction mixture of step D may further comprise sodium cyanoborohydride as a reducing agent; and step D may be conducted in the presence of N,N-dimethylformamide and at a temperature of about 23° C. under nitrogen. The O-dealkylating agent of step E may be hydrobromic acid; the weight ratio of the O-dealkylating agent to the compound of Formula (V) may be about 220:1; and step E may be conducted at a temperature of about 110° C. under nitrogen. In an exemplary, the compound of Formula (VI) is 3-[(1R,2R)-3-(dimethyamino)-1-ethyl-2-methylpropyl]phenol) (i.e., tapentadol).

In a particular embodiment, the process disclosed herein may be used to produce a compound of Formula (VIa), as depicted below:

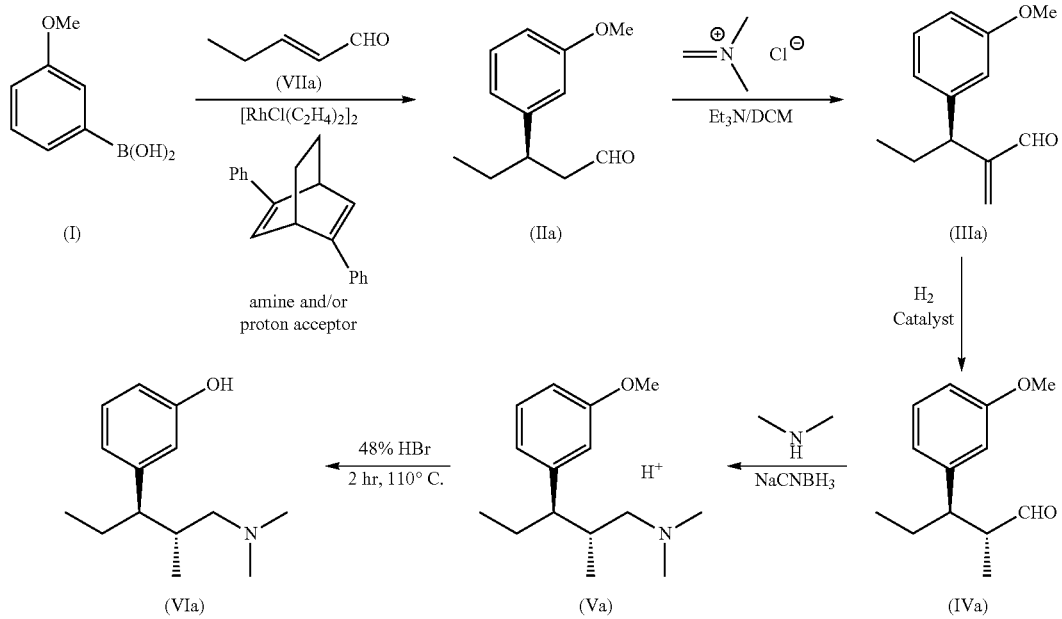

In one embodiment, Steps A through E proceed directly from one another in the order shown above. "Proceed directly," as used herein, means that intermediate reactions that add to or alter the chemical structure of the shown transformation are not used. For example, in one embodiment, Step B proceeds directly from Step A without any further steps that change the structure of the compound produced by Step A; Step C proceeds directly from Step B without any further steps that change the structure of the compound produced by Step B; Step D proceeds directly from Step C without any further steps that change the structure of the compound produced by Step C, and Step E proceeds directly from Step D without any further steps that change the structure of the compound produced by Step D. A skilled artisan understands that chemical workups and the like may be used between steps without parting from the meaning of "proceed directly."

(II) A 3-Step Process for the Preparation of Compound (VI)

Another aspect of the present disclosure provides a 3-step process for preparing a compound of Formula (VI). Performing the asymmetric 1,4-addition reaction using a compound of Formula (VIII) permits the elimination of two process steps, i.e., α-alkene formation and then subsequent reduction of the double bond. Moreover, it was discovered that a significant improvement in the selectivity of the desired (2R,3R) diastereomer was achieved by adding an amine during the asymmetric 1,4-addition reaction using compound of Formula (VIII) in the 3-Step Process.

The process comprises contacting a compound of Formula (I) with a compound of Formula (VIII) in the presence of a transition metal catalyst and a chiral ligand, and optionally in the presence of an amine, to form a compound of Formula (IX); contacting the compound of Formula (IX) with a secondary amine of Formula (X) to form a compound of Formula (V); and contacting the compound of Formula (V) with an O-dealkylating agent to form the compound of Formula (VI) according to Reaction Scheme 2.

Each of R, $R^1$, $R^2$, $R^3$, $R^4$, $R^5$, $R^7$, $R^8$, $R^{10}$, $R^{11}$, $R^{13}$, $R^{14}$, $R^{20}$, and $R^{21}$ are as defined above. In some embodiments, $R^{12}$ may be alkyl, substituted alkyl, aryl, or substituted aryl. In certain embodiments, $R^{12}$ may be $C_1$-$C_{10}$ alkyl or substituted $C_1$-$C_{10}$ alkyl. In certain embodiments, $R^{12}$ may be methyl, ethyl, propyl, isopropyl, butyl, tertbutyl, pentyl, or hexyl. In specific embodiments, $R^{12}$ may be methyl.

Reaction Scheme 2

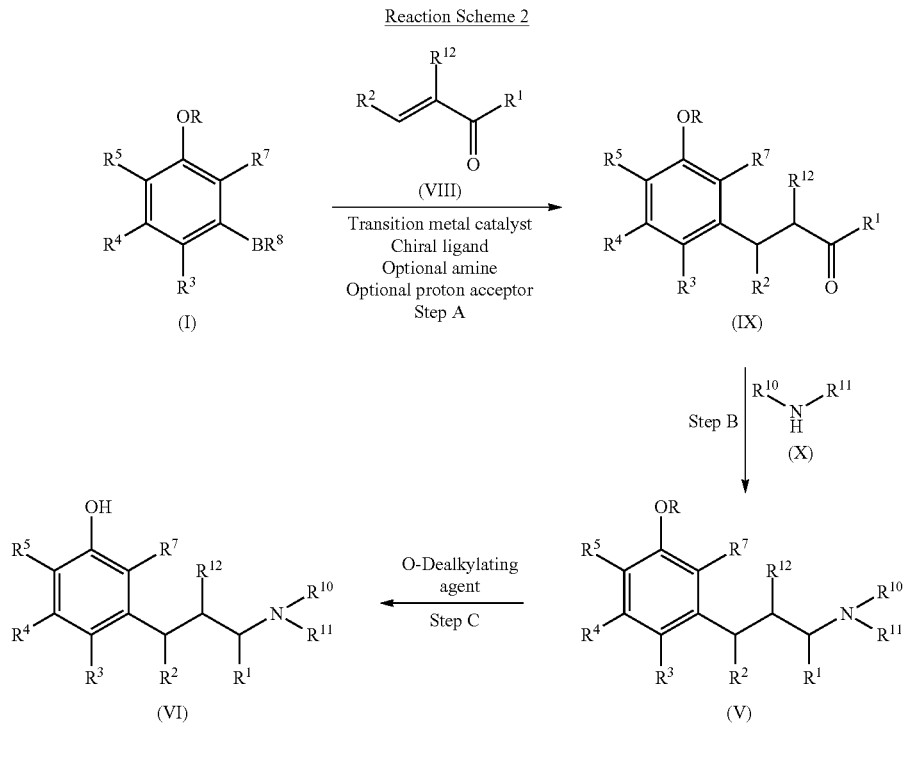

wherein:
R is alkyl or alkyl substituted with other than aryl;
$R^1$ is hydrogen, alkyl, or substituted alkyl;
$R^2$ is hydrocarbyl or substituted hydrocarbyl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl;
$R^8$ is

—O—$(CR^{13}R^{14})_n$—O—, or trihalo;
$R^{10}$ and $R^{11}$ are independently hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{12}$ is hydrocarbyl or substituted hydrocarbyl;
$R^{13}$ and $R^{14}$ are independently hydrogen, hydrocarbyl, substituted hydrocarbyl, or boron containing moiety;
$R^{20}$ and $R^{21}$ are independently hydrogen, hydrocarbyl, or substituted hydrocarbyl; and
n is an integer of 1 or greater.

(a) Step A of the 3-Step Process

Step A involves contacting a compound of Formula (I) with a compound of Formula (VIII) in the presence of a transition metal catalyst and a chiral ligand (and optionally, an amine) to form a compound of Formula (IX).

(i) Phenyl Boronic Compound

The compound of Formula (I) may be as described in section (I)(a)(i).

(ii) α/β-Unsaturated Carbonyl Compound

The α,β-unsaturated carbonyl compound of Formula (VIII) comprising $R^1$, $R^2$ and $R^{12}$ is detailed above. In some embodiments, $R^1$, $R^2$, and $R^{12}$ may be hydrogen, alkyl, or substituted alkyl. In certain embodiments, $R^1$ may be hydrogen and $R^2$ and $R^{12}$ may be alkyl or substituted alkyl. In preferred embodiments in which $R^1$ is hydrogen, $R^2$ is ethyl, and $R^{12}$ is methyl the compound may be trans-2-methyl-2-pentenal.

In general, the molar ratio of the compound of Formula (I) to the compound of Formula (VIII) may range from about 1:0.5 to about 1:2.0. In various embodiments, the molar ratio of the compound of Formula (I) to the compound of Formula (VIII) may range from about 1:0.5 to about 1:0.6, from about 1:0.6 to about 1:0.8, from about 1:0.8 to about 1:1, from about 1:1 to about 1:1.2, from about 1:1.2 to about 1:1.4, from about 1:1.4 to about 1:1.6, from about 1:1.6 to about 1:1.8, or from about 1:1.8 to about 1:2.0. In one exemplary embodiment, the molar ratio of the compound of Formula (I) to the compound of Formula (VIII) may range from about 1:0.8 to about 1:1.4. In another exemplary embodiment, the molar ratio of the compound of Formula (I) to the compound of Formula (VIII) may be about 1:1.

(iii) Transition Metal Catalyst

A wide variety of transition metal catalysts may be used in the process to catalyze the 1,4-addition of step A. The transition metal catalysts that may be used in this step are detailed in section (I)(a)(iii). An exemplary transition metal complex is $[RhCl(C_2H_4)_2]_2$.

The molar ratio of the compound of Formula (I) to the transition metal catalyst may vary depending, for example, on the nature of the catalyst. In general, the molar ratio of the compound of Formula (I) and the transition metal catalyst complex will range from about 1:0.0001 to about 1:0.05. In certain embodiments, the molar ratio of the compound of Formula (I) to the transition metal catalyst may range from about 1:0.0001 to about 1:0.001, from about 1:0.001 to about 1:0.005, from about 1:0.005 to about 1:0.025, or from about 1:0.025 to about 0.05. In one exemplary embodiment, the molar ratio of the compound of Formula (I) to the transition metal catalyst may range from about 1:0.0025 to about 1:0.05. In another exemplary embodiment, the molar ratio of the comprising Formula (I) to the transition metal catalyst may range from about 1:0.01 to about 1:0.02. In a further exemplary embodiment, the molar ratio of the phenyl boronic compound to the transition metal catalyst may be about 1:0.007.

(iv) Chiral Ligand

As detailed above in section (I)(a)(iv), chiral ligands may be any organic ligand that can complex with a catalytic metal and has at least one stable chiral center, and, in exemplary embodiments, two chiral centers. In an exemplary embodiment, the chiral ligand may be 2,5-diphenylbicyclo[2.2.2]octa-2,5-diene (Ph-bod*), for example (1R,4R)-2,5-diphenylbicyclo[2.2.2]octa-2,5-diene ((R,R)-Ph-bod*), (1R,4S)-2,5-diphenylbicyclo[2.2.2]octa-2,5-diene ((R,S)-Ph-bod*), (1S,4R)-2,5-diphenylbicyclo[2.2.2]octa-2,5-diene ((S,R)-Ph-bod*) or (1S,4S)-2,5-diphenylbicyclo[2.2.2]octa-2,5-diene ((S,S)-Ph-bod*).

The weight ratio of the transition metal catalyst to the chiral ligand is detailed in section (I)(a)(iii).

(v) Optional Proton Acceptor

The reaction mixture, as detailed herein, may also comprise a proton acceptor. The proton acceptor that may be used in this step are detailed in section (I)(a)(v). An exemplary proton acceptor is potassium hydroxide. Suitable weight ratios of the compound of Formula (I) to the proton acceptor are detailed in section (I)(a)(v).

(vi) Optional Amine

The amine that may be used in this step are detailed in section (I)(a)(vi). An amine is 4-methylmorpholine. Suitable weight ratios of the compound of Formula (I) to the amine are detailed in section (I)(a)(vi).

(vii) Solvent

The reaction mixture, as detailed herein, may also comprise a solvent. The solvent can and will vary depending on the starting substrates, the transition metal catalyst, and the chiral ligand used in the process. The solvent may be a polar protic solvent, a polar aprotic solvent, a non-polar solvent, or combinations thereof. Suitable solvents may be chosen from those described in section (I)(a)(vii). Suitable ratios of the solvent to the compound of Formula (I) are also detailed above in section (I)(a)(vii).

(viii) Reaction Conditions

In general, the reaction of step A will be conducted at a temperature that ranges as specified in section 1(a)(viii).

The compound of Formula (IX) may have a yield of at least about 25%. In various embodiments, the compound of Formula (IX) may have a yield of at least about 30%, of at least about 40%, of at least about 50%, at least about 70%, at least about 75%, at least about 80%, at least about 85%, at least about 90%, at least about 95%, or at least about 99%.

The compound of Formula (IX) may have a percent of diastereomeric excess (DE %) greater than 20%, at least about 30%, at least about 40%, at least about 50%, at least about 60%, at least about 70%, at least about 80%, at least about 90%, at least about 95%, or at least about 99.5%.

The compound of Formula (IX) with the addition of the amine may have a percent of diastereomeric excess (DE %) greater than 20%, at least about 30%, at least about 40%, at least about 50%, at least about 60%, at least about 70%, at least about 80%, at least about 90%, at least about 95%, at least about 99%, or at least about 99.5%.

(b) Step B of the 3-Step Process

The next step of the process comprises contacting the compound of Formula (IX) with a secondary amine of Formula (X) to form the compound of Formula (V) in accordance with Step D as described in section (I)(d). The compound of Formula (X), reducing agent, solvent and reaction conditions for Step B of the process are as described in section (I)(d). In order to prevent additional side products, the compound of Formula (IX) from Step A may need to be isolated before proceeding to Step B.

(c) Step C of the 3-Step Process

Step C comprises contacting the compound of Formula (V) with an O-dealkylating agent to form the compound of Formula (VI). The O-dealkylating reagent, solvent, and reaction conditions are as described in section (I)(e). Step C may proceed directly from Step B.

(d) Exemplary Embodiments

In exemplary embodiments, R may be methyl; each of $R^3$, $R^4$, $R^5$, and $R^7$ may be hydrogen; $R^1$ may be hydrogen; $R^2$ may be ethyl; $R^{12}$ may be methyl; and both $R^{10}$ and $R^{11}$ may be methyl. The compound of Formula (I) may be m-methoxyphenylboronic acid, 3-methoxyphenyl trifluoroborate, 3-methoxyphenylboronic acid pinacol ester, 3-methoxyphenylboronic ester, or a compound derived from 3-methoxyphenylboroxine. The transition metal catalyst may be $[RhCl(C_2H_4)_2]_2$; the chiral ligand may be (1S,4S)-2,5-diphenylbicyclo[2.2.2]octa-2,5-diene; the proton acceptor may be potassium hydroxide; and the amine may be 4-methylmorpholine.

In some exemplary embodiments, the molar ratio of the compound of Formula (I) to the compound of Formula (VIII) may be about 1:1.15; the molar of the compound of Formula (I) to the transition metal catalyst may be about 1:0.007; the weight ratio of the transition metal catalyst to the chiral ligand may about 1:1.5; the molar ratio of compound of Formula (I) to the optional amine may be about 1:0.4; the molar ratio of the compound of Formula (I) to the optional proton acceptor may be 1:0.2; step A may be conducted in the presence of tetrahydrofuran and methanol at a temperature of about 23° C. under nitrogen; and the compound of Formula (IX) may have a yield of at least about 60%. The molar ratio of the secondary amine to the compound of Formula (IX) may be about 1:1; the reaction mixture of step B may further comprise sodium cyanoborohydride as a reducing agent; and step B may be conducted in the presence of N,N-dimethylformamide and at a temperature of about 23° C. under nitrogen. The O-dealkylating agent of step C may be hydrobromic acid; the weight ratio of the O-dealkylating agent to the compound of Formula (V) may be about 26:1; and step C may be conducted at a temperature of about 110° C. undernitrogen. In an exemplary, the compound of Formula (VI) is 3-[(1R,2R)-3-(dimethyamino)-1-ethyl-2-methylpropyl]phenol] (i.e., tapentadol).

In a particular embodiment, the process disclosed herein may be used to produce a compound of Formula (VIa), as depicted below:

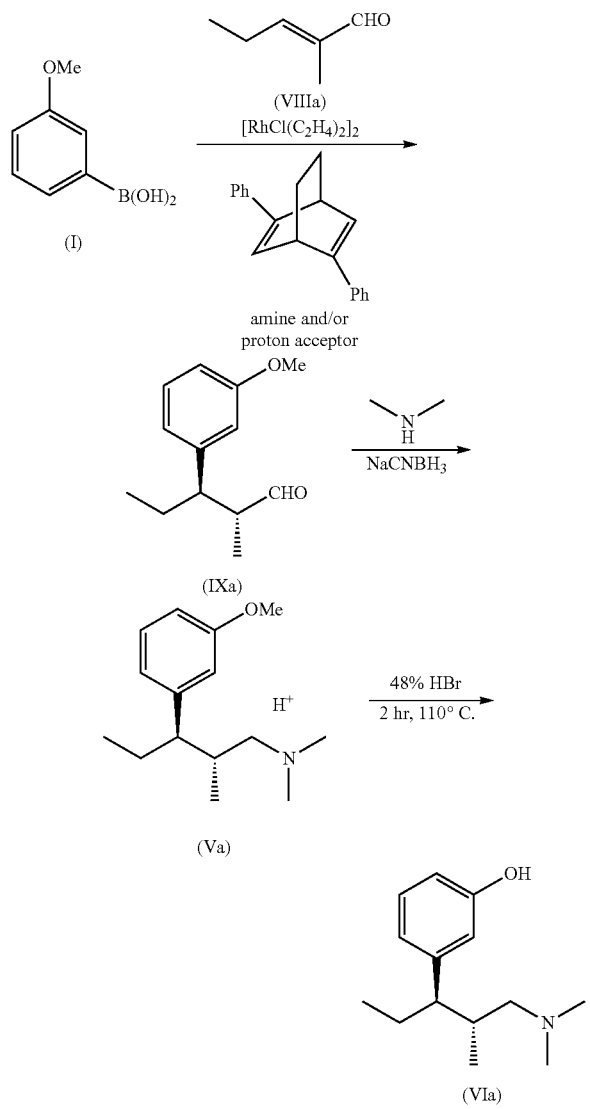

(III) Processes for the Preparation of a Compound of Formula (IIb)

In still another embodiment, the disclosure provides a process for preparing a compound of Formula (IIb). The process comprises contacting a compound of Formula (Ia) with a compound of Formula (VIIa) in the presence of a transition metal catalyst to form the compound of Formula (IIb) according to the following reaction scheme:

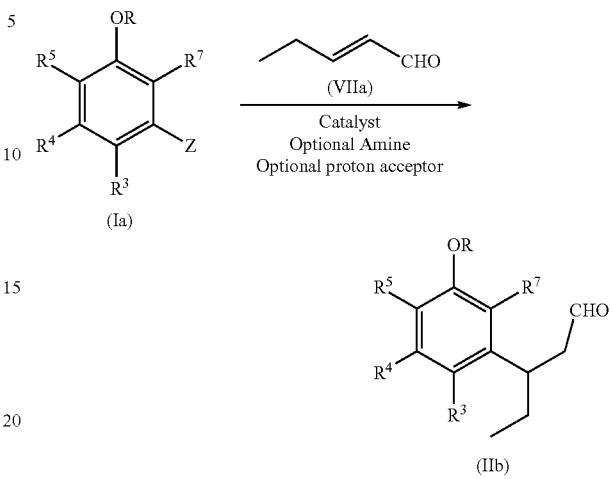

wherein:
Z is a boron containing moiety;
R is alkyl or alkyl substituted with other than aryl;
$R^3$, $R^4$, $R^5$, and $R^7$ are independently chosen from hydrogen, $OR^{20}$, $NR^{20}R^{21}$, $SR^{20}R^{21}$, halo, hydrocarbyl, and substituted hydrocarbyl;
$R^{20}$ and $R^{21}$ are independently chosen from hydrogen, hydrocarbyl, and substituted hydrocarbyl.

In one preferred embodiment, $R^3$, $R^4$, $R^5$, and $R^7$ are hydrogen. In another preferred embodiment, R is methyl. The amount of the compound of Formula (I)(a) to the compound of Formula (VIIa) may be as described in section (I)(a)(ii) for the compound of Formula (VII).

In one embodiment, the catalyst may be selected from those detailed in section (I)(a)(iii). In still another embodiment, the catalyst may be a rhodium (I) catalyst. In still other embodiments, the catalyst may be [RhCl(C₂H₄)₂]₂.

The reaction may further comprise addition of a chiral ligand. The chiral ligand may be preferably a diene ligand. Suitable ligands may be chosen from those listed in section (I)(a)(iv). In some embodiments, the ligand may be 2,5-diphenylbicyclo[2,2,2]octa-2,5-diene. The 2,5-diphenylbicyclo[2,2,2]octa-2,5-diene may be chosen from (1S,4S), (1R,4S), (1S,4R) and (1R,4R).

The reaction may further comprise an optional proton acceptor. Suitable proton acceptors may be chosen from those described in section (I)(a)(v).

The reaction may further comprise an optional amine. Suitable amines may be chosen from those described in section (I)(a)(vi).

The reaction may also be conducted in a solvent. Suitable solvents may be chosen from those described in section (I)(a)(vii). The reaction conditions may be as described in section (II)(a)(viii).

The compound of Formula (IIb) may have a yield of at least about 50%. In various embodiments, the compound of Formula (IIb) may have a yield of at least about 50%, at least about 55%, at least about 60%, at least about 65%, at least about 70%, at least about 75%, at least about 80%, at least about 85%, at least about 90%, at least about 95%, or at least about 99%. The stereochemistry of the compound of Formula (IIb) produced may be R configuration. The compound of Formula (IIb) may be produced with an enantiomeric excess (EE %) of at least about 50%, at least about 55%, at least about 60%, at least about 65%, at least about 70%, at least about 75%, at least about 80%, at least about 85%, at least about 90%, at least about 95%, at least about 99% or higher.

(IV) Processes for the Preparation of a Compound of Formula (IXb)

In still another embodiment, the disclosure provides a process for producing a compound of (IXb). The process comprises contacting a compound of Formula (Ia) with a compound of Formula (VIIIa) in the presence of a catalyst (and an optional amine) according to the following reaction scheme:

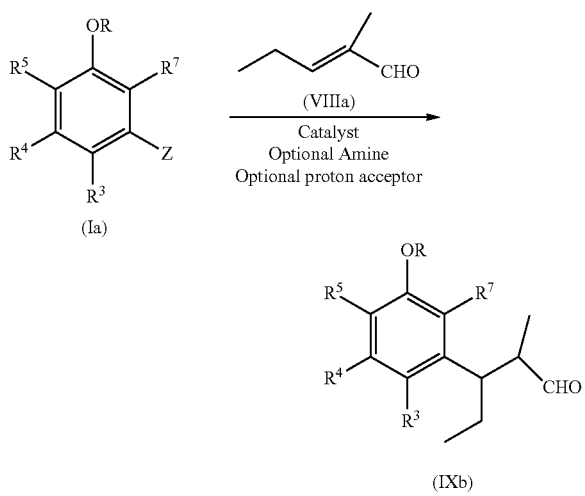

wherein:
Z is a boron containing moiety;
R is alkyl or alkyl substituted with other than aryl;
$R^3$, $R^4$, $R^5$, and $R^7$ are independently chosen from hydrogen, $OR^{20}$, $NR^{20}R^{21}$, $SR^{20}R^{21}$, halo, hydrocarbyl, and substituted hydrocarbyl; and
$R^{20}$ and $R^{21}$ are independently chosen from hydrogen, hydrocarbyl, and substituted hydrocarbyl.

In one preferred embodiment, $R^3$, $R^4$, $R^5$, and $R^7$ are hydrogen. In another preferred embodiment, R is methyl. The amount of the compound of Formula (Ia) and the compound of Formula (VIIIa) may be as described in section (II)(a)(ii) for the compound of Formula (VIII).

In one embodiment, the catalyst may be selected from those detailed in section (II)(a)(iii). In still another embodiment, the catalyst may be a rhodium (I) catalyst. In still other embodiments, the catalyst may be $[RhCl(C_2H_4)_2]_2$.

The reaction may further comprise addition of a chiral ligand. The ligand may be preferably a diene ligand. Suitable ligands may be chosen from those listed in section (II)(a)(iv). In some embodiments, the ligand is 2,5-diphenylbicyclo[2,2,2]octa-2,5-diene. The 2,5-diphenylbicyclo[2,2,2]octa-2,5-diene may be chosen from (1S,4S), (1R,4S), (1S,4R) and (1R,4R).

The reaction may be also conducted in the presence of a proton acceptor. Suitable proton acceptors may be chosen from those described in section (II)(a)(v).

The reaction may be also conducted in the presence of an amine. Suitable amines may be chosen from those described in section (II)(a)(vi).

The reaction may also be conducted in a solvent. Suitable solvents may be chosen from those described in Section (II)(a)(vii). The reaction conditions may be as described in Section (II)(a)(viii).

The compound of Formula (IXb) may have a yield of at least about 60%. In various embodiments, the compound of Formula (IXb) may have a yield of at least about 60%, at least about 65%, at least about 70%, at least about 75%, at least about 80%, at least about 85%, at least about 90%, at least about 95%, or at least about 99%. The compound of Formula (IXb) may be produced with a diastereomeric excess above 70% for a given diastereomeric configuration.

DEFINITIONS

The compounds described herein have asymmetric centers.

Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. Where the moiety is an oxygen atom (and hence, forming a protected hydroxy), exemplary protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. When the moiety is a nitrogen atom (and hence, forming a protecting amine) exemplary protecting groups include benzyl, p-methoxyphenyl (PMP), 3,4-dimethoxybenxyl (PMB)), n-silyl groups, esters (e.g., benzoate (Bz), carbonyl (e.g. p-methoxybenzyl carbonyl (Moz), tert-butyloxycarbonyl (BOC), 9-fluorenylmethyloxycarbonyl (FMOC)), acetyl, carbamates, n-silyl groups and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro and thio.

When introducing elements of the present disclosure or the exemplary embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

The following examples are included to demonstrate embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes may be made in the specific embodiments that are disclosed and still obtain a like or similar result without departing from the spirit and scope of the disclosure; therefore all matter set forth is to be interpreted as illustrative and not in a limiting sense.

Examples 1-5 exemplify embodiments of the five step process. Examples 6-10 exemplify embodiments of the three step process.

Example 1

Preparation of 3-(3-Methoxyphenyl) pentanal (2)

Trans-penten-2-al and 3-methoxyphenylboronic acid (1) were reacted to form 3-(3-methoxyphenyl)pentanal (2) via a catalytic asymmetric 1,4-addition reaction.

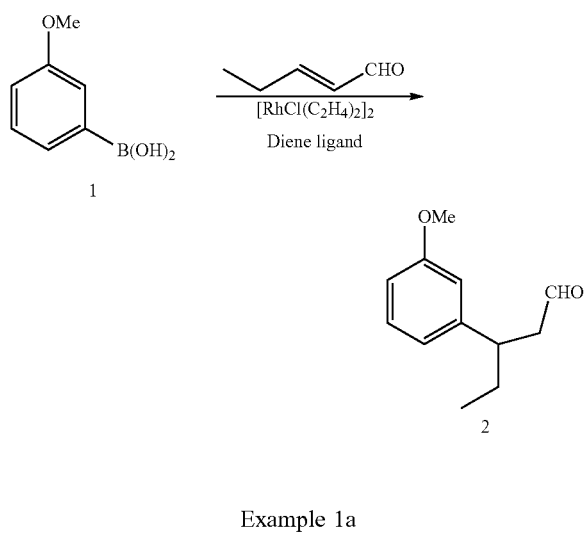

Example 1a

Synthesis of (R)-3-(3-Methoxyphenyl)pentanal

The mixture of 3-methoxyphenylboronic acid (1) (2.67 g, 17.5 mmol), trans-2-pentenal (1.50 g, 17.5 mmol), methanol (26.3 mL), tetrahydrofuran (THF, 6.5 mL), water (4.4 mL), di-μ-chlorotetraethylenerhodium (I) ([(RhCl(C$_2$H$_4$)$_2$]$_2$, 50.8 mg, 0.262 mmol), and (1S,4S)-2,5-diphenylbicyclo[2.2.2]octa-2,5-diene (74.6 mg, 0.288 mmol) under nitrogen was stirred at room temperature for 5 minutes, followed by adding potassium hydroxide (98.0 mg, 1.75 mmol); the resulting mixture was stirred under nitrogen at room temperature for one hour. The reaction was quenched by adding 50 mL saturated aqueous ammonium chloride solution (sat. aq. NH$_4$Cl). The resulting mixture was stirred at room temperature for 15 minutes. The product was extracted with ethyl acetate (3×70 mL), and the combined organic extracts were washed with sat. aq. NH$_4$Cl three times and brine once, and dried over anhydrous sodium sulfate. The drying reagent was filtered out and the filtrate was concentrated in vacuum to light brown oil. The crude product was further purified on silica gel column with 15/85 ethyl acetate/heptanes. The collected product was colorless oil, 3.5 g. GC-MS(EI$^+$): m/z=192.2; $^1$H NMR (CDCl$_2$CDCl$_2$) in δ ppm: 9.65 (t, J=2.1 Hz, 1H, CHO), 7.24 (dd, J=9.0 Hz, 7.5 Hz, 1H, aromatic proton), 6.82-6.76 (m, 3H, aromatic proton), 3.80 (s, 3H, OCH$_3$), 3.11-3.02 (m, 1H, CH), 2.70 (dd, J=9.3, 2.1 Hz, 2H, CH$_2$), 1.74-1.63 (m, 2H, CH$_2$), 0.83 (t, J=7.2 Hz, 3H, CH$_3$). $^{13}$C NMR (CDCl$_2$CDCl$_2$) in δ ppm: 201.5, 159.8, 145.7, 129.4, 119.9, 113.5, 111.4, 55.0, 50.0, 41.7, 29.4, 11.7.

Example 1b

Synthesis of (R)-3-(3-methoxyphenyl)pentanal

To the reaction flask under nitrogen was charged with 3-methoxyphenylboronic acid (10.68 g), trans-2-pentenal (6.0 g), methanol (105 mL), tetrahydrofuran (26 mL), water (17.6 mL), Di-μ-chlorotetraethylene dirhodium (1)(100 mg), and (1S,4S)-2,5-diphenylbicyclo[2,2,2]octa-2,5-diene (150 mg), followed by adding potassium hydroxide powder (392 mg). The resulting mixture was stirred at room temperature for 1.5 hours. The reaction was quenched by adding 250 mL saturated ammonium chloride aqueous solution. After stirring for 15 minutes, the product was extracted with ethyl acetate (3×160 mL). The combined organic extracts were washed with saturated ammonium chloride (2×250 mL), brine (250 mL) and then dried over anhydrous sodium sulfate. After filtered the drying reagent, the filtrate was concentrated under vacuum. The brown residue was further purified on silica gel column with 15:85 ethyl acetate/heptanes mixture as elute. The column chromatograph purification provided 10.8 g clear oil, purity was 84%, the yield was 80%.

Example 1c

Synthesis of (R)-3-(3-methoxyphenyl)pentanal

To the reaction flask under nitrogen was charged with (1S,4S)-2,5-diphenylbicyclo[2,2,2]octa-2,5-diene (4.8 mg), Di-μ-chlorotetraethylene dirhodium (1)(3.3 mg), 3-methoxyphenylboronic acid (0.5 g), methanol (7.6 mL), trans-2-pentenal (0.3 g). The resulting mixture was stirred at room temperature for 15 minutes; then to the reaction was added 4-methylmorpholine (0.15 mL). The resulting mixture was stirred at room temperature for 4 hours. The reaction was cooled in ice bath, then quenched by adding 15% acetic acid aqueous solution (7.5 mL), followed by adding 10 mL brine. The product was extracted with toluene (3×15 mL). The combined organic extracts were washed with brine (3×15 mL) and then dried over anhydrous magnesium sulfate. The drying reagent was filtered. The filtrate was concentrated in vacuum. The residue was purified on silica gel column with 95:5 Heptane/EtOAc mixture. The collected fraction was concentrated in vacuum and provided 0.43 g oil with 95% purity, yield was 65%.

Example 1d

Synthesis of (S)-3-(3-methoxyphenyl)pentanal

To the reaction flask under nitrogen was added 3-methoxyphenylboronic acid(5.34 g), trans-2-pentenal (3.0 g), methanol (53 mL), tetrahydrofuran (13 mL), water (8.8 mL), (1R,4R)-2,5-diphenylbicyclo-[2,2,2]octa-2,5-diene (150 mg), and di-μ-chlorotetraethylene dirhodium (I)(51 mg), followed by adding potassium hydroxide powder (196 mg); the resulting mixture was stirred under nitrogen at room temperature for one hour; the reaction was quenched by adding 100 ml saturated ammonium chloride solution. The product was extracted with ethyl acetate (3×150 mL); the combined organic extracts were washed with brine and dried over anhydrous sodium sulfate. After filtered the drying reagent, the filtrate was concentrated in vacuum. The residue was purified on silica gel column with 1:9 ethyl acetate/heptanes mixture as elute. The product was obtained as 5.2 g light yellow oil with 75% purity. Yield was 58%.

Example 1e

Synthesis of (S)-3-(3-methoxyphenyl)pentanal with chiral purity

To the reaction flask was added (1S,4S)-2,5-diphenylbicyclo[2.2.2]octa-2,5-diene (27.9 mg), di-μ-chlorotetraethylenerhodium (I) ([(RhCl(C$_2$H$_4$)$_2$]$_2$, 19 mg), 3-methoxyphenylboronic acid (1) (1.0 g), methanol (9.9 mL), tetrahydrofuran (2.43 mL), water (1.65 mL), and trans-2-pentenal (0.56 g). The resulting mixture was stirred at room temperature for 5 minutes; potassium hydroxide powder (36.7 mg) was added. The resulting mixture was stirred under nitrogen at room temperature for one hour. The reaction was quenched by adding saturated aqueous ammonium chloride solution (sat. aq. NH₄Cl). The resulting mixture was stirred at room temperature for 15 minutes. The product was extracted with ethyl acetate, and the combined organic extracts were washed with sat. aq. NH₄Cl three times and brine once, and then dried over anhydrous sodium sulfate. The drying reagent was filtered out and the filtrate was concentrated in vacuum to light brown oil. The crude product was further purified using silica gel chromatography eluted with ethyl acetate/heptane mixture. The collected product was colorless oil, 0.78 g. Chiral GC analysis indicated the product had 95.3% chiral purity and ee=90.6%.

Example 2

Preparation of 3-(3-methoxyphenyl)-2-methylenepentanal (3)

The pentanal (3) was α-methylenated with dimethylmethyleneiminium chloride in the presence of organic base triethylamine.

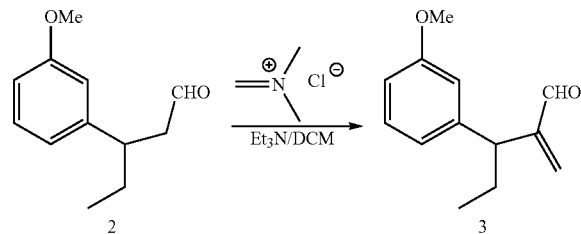

Example 2a

Synthesis of (S)-3-(3-methoxyphenyl)-2-methylenepentanal

To the solution of (S)-3-(3-methoxyphenyl)pentanal (1.0 g, 5.2 mmol) in 40 mL dichloromethane was added N,N-dimethylmethyleneiminium chloride (1.17 g, 12.5 mmol) and triethylamine (1.55 mL, 10.2 mmol). The resulting solution was stirred under nitrogen overnight. To this reaction was added 80 mL saturated sodium bicarbonate solution, the organic phase was separated, and the aqueous phase was extracted with dichloromethane (3×60 mL). The combined organic extracts were washed with saturated ammonium chloride twice, saturated brine once, and then dried over anhydrous sodium sulfate. The drying reagent was filtered out; the filtrate was evaporated to oil; the crude product was purified on silica gel column chromatograph with 15:85 EtOAc/Heptane; the collected fraction gave 0.72 g colorless oil after removing volatiles. GC-MS(EI⁺), m/z=204.2; ¹H NMR (CDCl₂CDCl₂) in δ ppm: 9.52 (s, 1H, CHO), 7.20 (dd, J=7.8, 0.6 Hz, 1H, aromatic proton), 6.84-6.75 (m, 3H, aromatic protons), 6.38 (d, J=0.9 Hz, 1H, =CH), 6.13 (d, J=0.9 Hz, 1H, =CH), 3.79 (s, 3H, OCH₃), 3.78-3.70 (t, J=8.1 Hz, 1H), 1.90-1.82 (m, 2H, CH₂), 0.88 (t, J=7.2 Hz, 3H, CH₃); ¹³C NMR (CDCl₂CDCl₂) in δ ppm: 193.8, 159.7, 152.9, 144.3, 133.6, 129.2, 120.4, 114.0, 111.3, 54.9, 44.8, 27.1, 12.2.

Example 2b

Synthesis of (S)-3-(3-methoxyphenyl)-2-methylenepentanal

To the flask under nitrogen was charged with (S)-3-(3-methoxyphenyl)pentanal (5.2 g) in 200 mL of dichloromethane was added N,N-dimethylmethyleneiminium chloride (6.1 g) and triethylamine (8 mL). The resulting solution was stirred under nitrogen overnight. The reaction was quenched by adding 200 mL saturated sodium bicarbonate aqueous solution. After stirring for 30 min, the product was extracted with dichloromethane (3×100 mL). The combined organic extracts were washed with water and dried over anhydrous sodium sulfate. After filtering out the drying reagent, the filtrate was concentrated under vacuum; the residue was further purified on silica gel column with 15:85 ethyl acetate/heptanes and it provided 5.2 g light yellow oil with 91% purity and 85% yield.

Example 2c

Synthesis of (R)-3-(3-methoxyphenyl)-2-methylenepentanal

To the solution of (R)-3-(3-methoxyphenyl)pentanal (10.8 g) in 320 mL of dichloromethane was added N,N-dimethylmethyleneiminium chloride (12.6 g) and triethylamine (16.7 mL). The resulting solution was stirred under nitrogen overnight. The reaction was quenched by adding 150 mL saturated ammonium chloride aqueous solution. After stirring for 30 min, the product was extracted with dichloromethane (2×150 mL). The combined organic extracts were washed with 1N hydrochloric acid aqueous solution (2×150 mL). The acidic washings were combine with aqueous phase; the combined aqueous phases were neutralized with 3 N HCl until pH=8.0. The product was extracted with dichloromethane (3×150 mL). The combined organic extracts were further combined with organic phase separated earlier. The combined organic solution was washed with brine and dried over anhydrous sodium sulfate. After filtering out the drying reagent, the filtrate was concentrated under vacuum; the residue was further purified on silica gel column with 2:8 ethyl acetate/heptanes and it provided 8.8 g clear oil with 95% purity and 81% yield.

Example 3

Preparation of 3-(3-Methoxyphenyl)-2-methylpentanal (4)

The α,β-unsaturated anal (3) was hydrogenated in the presence of a transition metal catalyst (palladium on carbon) to introduce the α-methyl group.

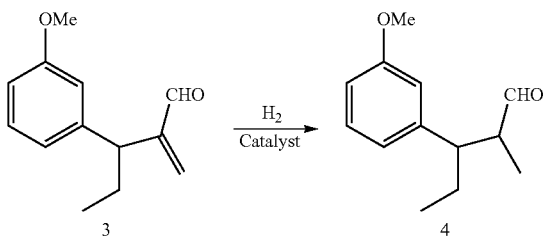

Example 3a

Synthesis of (2R,3R)-/(2S,3R)-(3-(3-Methoxyphenyl)-2-methylpental isomers

A Parr reaction bottle was charged with 90 mg of (3R)-3-(3-methoxyphenyl)-2-methylenepentanal (3) (0.44 mmol), 10 mL ethyl acetate, and 10 mg of 5% Pd/C (0.0050 mmol of Pd, 1 mol % catalytic loading). The resulting mixture was shaken under 50 psi H₂ for 3 hours. The reaction mixture was filtered through diatomaceous earth (Celite®) and the residue was washed with additional ethyl acetate. After removing the volatiles, 85 mg (0.41 mmol) of colorless oil remained. Combined yield: 94% yield. GC-MS (EI+): m/z=206.1 (calculated), 206.2 (observed in two peaks). The ratio of (2R,3R)-/(2S,3R)-isomers was 62/38.

Example 4

Preparation of 3-(3-Methoxyphenyl)-N,N,2-trimethylpentan-1-amine (5)

The dimethylamino group was introduced at the aldehyde (4) via reductive-amination using dimethylamine and a reducing agent.

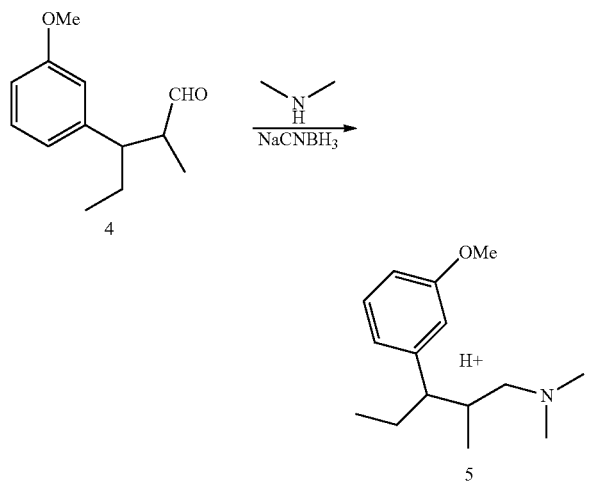

Example 4a

Synthesis of (2R,3R)-/(2S,3R)-3-(3-Methoxyphenyl)-N,N,2-trimethylpentan-1-amines To the flask containing 0.73 g of 3-(3-methoxyphenyl)-2-methylpentanal (4) with the 35/65 ratio of (2R,3R)-/(2S,3R)-isomers was added 24 mL of N,N-dimethylformamide, 0.93 g dimethylamine hydrochloride, and 0.77 g of sodium cyanoborohydride; the resulting mixture was stirred under nitrogen overnight. The reaction was quenched by adding 30 mL saturated aqueous NaHCO₃ solution. The product was extracted with ethyl acetate (3×50 mL). The combined organic extracts were washed with brine and dried over anhydrous sodium sulfate. After removing the volatiles, 1.05 g clear oil was obtained. LC-MS (ES), M+H⁺=236.20 (calculated), 236.48 (observed in first peak) and 236.47 (observed in second peak). The ratio of (2R,3R)-/(2S,3R)-isomers was 34/66 in the product.

Example 5

Preparation of 3-(3-hydroxyphenyl)-N,N-2-trimethylpentan-1-amine (6)

A final O-demethylation on the amine compound (5) yielded tapentadol (6).

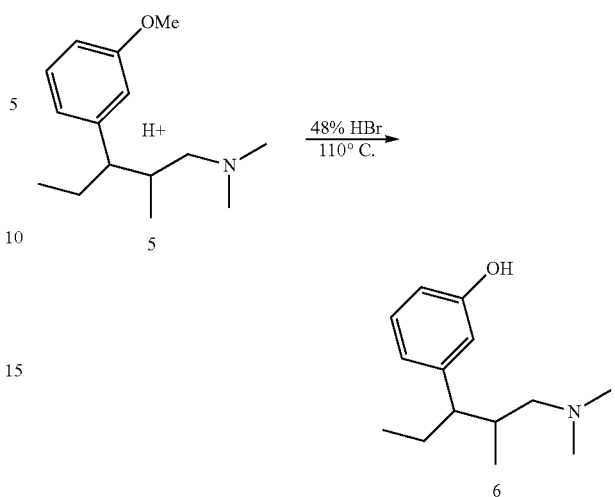

Example 5a

Synthesis of (2R,3R)-/(2S,3R)-3-(3-hydroxyphenyl)-N,N-2-trimethylpentan-1-amines To the flask containing 120 mg light oil of 3-(3-methoxyphenyl)-N,N-2-trimethylpentan-1-amine (5) (the ratio of (2R,3R)-/(2S,3R)-isomers was 30/70) was added 10 mL of concentrated hydrobromic acid (conc. HBr). The resulting solution was heated to 110° C. under nitrogen for two hours. After cooling to room temperature, the reaction was further cooled in an ice bath for 15 minutes, and the pH of the cooled solution was adjusted to 8 with sodium bicarbonate. The product was then extracted with dichloromethane (3×30 mL). The combined organic extracts were dried over anhydrous sodium sulfate. The drying reagent was filtered out, and after removing the volatiles, the residue was dissolved in 5 mL of 2-butanone. The resulting solution was bubbled with HCl gas and a solid was precipitated (70 mg, 0.315 mmol) during the bubbling. Combined yield: 62%. LC-MS (ES⁻): M+H⁺=222.19 (calculated), 222.29 (observed in first peak), 222.27 (observed in second peak). The ratio of (2R,3R)-/(2S,3R)-isomers was 30/70 in the product.

Example 6

Preparation of 2-Methyl-3-(3-Methoxyphenyl)pentanal

Trans-2-methyl-2-pentenal and 3-methoxyphenylboronic acid were reacted in the presence of a proton acceptor via catalytic asymmetric 1,4-addition reaction.

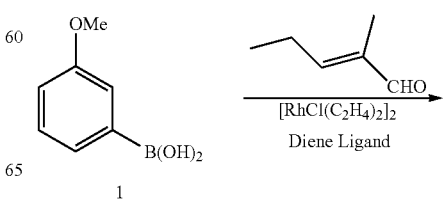

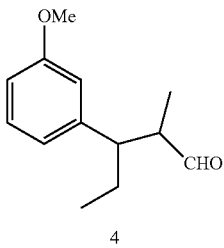

4

Example 6a

Synthesis of (2R,3R)- and (2S,3R)-3-(3-methoxyphenyl)-2-methylpentanals

To the reaction flask under nitrogen was charged with 3-methoxyphenylboronic acid (10 g), (1S,4S)-2,5-diphenylbicyclo[2,2,2]octa-2,5-diene(285 mg), 125 mL of tetrahydrofuran and methanol mixture (THF/MeOH=1:4), and trans-2-methyl-2-pentenal(7.5 g), followed by adding di-μ-chlorotetraethylene dirhodium (I) (190 mg). After the resulting solution was stirred at room temperature for 6 min, a potassium hydroxide aqueous solution, prepared by adding 435 mg 90% potassium hydroxide into 18 mL of water, was added to the reaction. The resulting solution was stirred at room temperature overnight. The reaction was quenched by adding 200 mL of 0.5 N hydrochloride solution. After stirring for 15 minutes, the product was extracted with ethyl acetate (3×180 mL). The combined organic extracts were washed with 0.5 N aqueous HCl solution (3×150 ml), water and dried over anhydrous sodium sulfate. After filtered the drying reagent, the filtrate was concentrated under vacuum; it gave 12.6 g stick brown oil, the crude material has 78.2% purity based on LC analysis; the (2R,3R)-/(2S,3R) isomer ratio was 65:35. The crude yield was 72.3%.

Small portion of the crude product was further separated on silica gel column with 1:19 EtOAc/heptanes as mobile phase; the first fraction was (2S,3R)-3-(3-methoxyphenyl)-2-methylpentanal isomer; the second fraction was (2R,3R)-3-(3-methoxyphenyl)-2-methylpentanal isomer. The separated isomers were characterized with NMR.

(2S,3R)-3-(3-methoxyphenyl)-2-methylpentanal $^1$H NMR (CDCl$_3$) in δ ppm: 9.66 (d, J=3.0 Hz, 1H, aldehyde proton), 7.22 (t, J=4.5 Hz, 1H, aromatic proton), 6.78-6.67 (m, 3H, aromatic proton), 3.79 (s, 3H, OCH$_3$), 2.78-2.70 (m, 1H, CH), 2.60-2.53 (m, 1H, CH), 1.75-1.68 (m, 2H, CH$_2$), 0.87 (d, J=6.9 Hz, 3H, CH$_3$), 0.76 (t, J=7.5 Hz, 3H, CH$_3$); $^{13}$CNMR(CDCl$_3$) in δ ppm: 205.0, 159.7, 143.1, 129.4, 120.9, 114.5, 111.5, 55.1, 51.9, 48.6, 27.1, 12.3, 12.2.

(2R,3R)-3-(3-methoxyphenyl)-2-methylpentanal $^1$H NMR (CDCl$_3$) in δ ppm: 9.55 (d, J=2.1 Hz, 1H, aldehyde proton), 7.25 (t, J=3.3 Hz, 1H, aromatic proton), 6.78-6.70 (m, 3H, aromatic proton), 3.78 (s, 3H, OCH$_3$), 2.79-2.76 (m, 1H, CH), 2.64-2.58 (m, 1H, CH), 1.76-1.69 (m, 1H, CH), 9.11 (d, J=6.9 Hz, 3H, CH$_3$), 0.81 (t, J=7.5 Hz, 3H, CH$_3$). $^{13}$C NMR (CDCl$_3$) in δ ppm: 204.9, 159.7, 143.7, 129.5, 120.7, 114.5, 111.5, 55.1, 51.7, 48.7, 24.8, 11.9, 11.4.

Example 6b

Synthesis of (2S,3S)-2-Methyl-3-(3-Methoxyphenyl)pentanal

To a reaction flask were charged 3-methoxyphenylboronic acid (1.0 g), trans-2-methyl-2-pentenal (0.73 g), MeOH (9.8 mL), THF (2.4 mL), (1R,4R)-2,5-diphenylbicyclo[2,2,2]octa-2,5-diene (28 mg), water (1.7 mL), and di-μ-chlorotetraethylene dirhodium(I) (19 mg), followed by adding potassium hydroxide (39 mg); the resulting mixture was stirred under nitrogen at room temperature for one hour. The reaction was quenched with 30 mL saturated sodium bicarbonate. The product was extracted with ethyl acetate (3×60 mL); the combined organic extracts were washed with brine and dried over anhydrous sodium sulfate; after filtering out the drying reagent, the filtrate was concentrated under vacuum. The resulting residue was purified on silica gel column with 15/85 EtOAc/heptanes. It produced 0.78 g colorless oil, yield=57%. The ratio of (2S,3S)-/(2R,3S)-isomers was 59/41 in the product.

Example 6c

Synthesis of (2R,3R)-2-Methyl-3-(3-Methoxyphenyl)pentanal

To a reaction flask were charged 3-methoxyphenylboronic acid (0.5 g), trans-2-methyl-2-pentenal (0.37 g), MeOH (5 mL), THF (1.2 mL), (1S,4S)-2,5-diphenylbicyclo[2,2,2]octa-2,5-diene (14 mg), water (0.9 mL), and di-μ-chlorotetraethylene dirhodium(I) (9.5 mg), followed by adding potassium carbonate (45 mg). The resulting mixture was stirred under nitrogen at room temperature overnight; the reaction was then quenched with 30 mL saturated sodium bicarbonate for 30 minutes. The product was extracted with ethyl acetate (3×60 mL); the combined organic extracts were washed with brine and dried over anhydrous sodium sulfate. After filtering out the drying reagent, the filtrate was concentrated under vacuum; the resulting residue was purified on silica gel column with a mixture of 15/85 EtOAc/heptanes. It produced 0.44 g colorless oil, yield=65%; the ratio of (2R,3R)-/(2S,3R)-isomers was 59/41 in the product.

Example 6d

Synthesis of 2-Methyl-3-(3-Methoxyphenyl)pentanal

To a reaction flask were charged 3-methoxyphenylboronic acid (0.5 g), trans-2-methyl-2-pentenal (0.37 g), MeOH (5 mL), THF (1.2 mL), (1S,4S)-2,5-diphenylbicyclo[2,2,2]octa-2,5-diene (14 mg), water (0.9 mL), and di-μ-chlorotetraethylene dirhodium(I) (9.5 mg), followed by adding sodium phosphate (53 mg), the resulting mixture was stirred under nitrogen at room temperature overnight; then, the reaction was quenched with 30 mL saturated sodium bicarbonate for 30 minutes. The product was extracted with ethyl acetate (3×60 mL); the combined organic extracts were washed with brine once and dried over anhydrous sodium sulfate; after filtering out the drying reagent, the filtrate was concentrated under vacuum; the resulting residue was purified on silica gel column with 15/85 EtOAc/heptanes. It produced 0.51 g colorless oil, yield=75%; the ratio of (2R.3R)-/(2S,3R)-isomers was 58/32 in the product.

Example 6e

Synthesis of
(2R,3R)-3-(3-methoxyphenyl)-2-methylpentanal

To a reaction flask were charged 3-methoxyphenylboronic acid (1.0 g), trans-2-methyl-2-pentenal (0.73 g), MeOH (9.8 mL), THF (2.4 mL), (1S,4S)-2,5-diphenylbicyclo[2,2,2]octa-2,5-diene (28 mg), water (1.7 mL), and di-μ-chlorotetraethylene dirhodium (I) (19 mg), followed by adding potassium hydroxide (39 mg); the resulting mixture was stirred under nitrogen at room temperature for one hour; then, the reaction was quenched with 30 mL saturated sodium bicarbonate. The product was extracted with ethyl acetate (3×60 mL); the combined organic extracts were washed with brine and dried over anhydrous sodium sulfate; after filtering out the drying reagent, the filtrate was concentrated in vacuum; the resulting residue was purified on silica gel column with 15/85 EtOAc/heptanes. It produced 0.52 g colorless oil with 72% purity (~28% yield); the ratio of (2R,3R)-/(2S,3R)-isomers was 62:38 in the product.

Example 6f

Synthesis of
(2S,3S)-3-(3-methoxyphenyl)-2-methylpentanal

To a reaction flask were charged 3-methoxyphenylboronic acid (1.0 g), trans-2-methyl-2-pentenal (0.73 g), MeOH (9.8 mL), THF (2.4 mL), (1R,4R)-2,5-diphenylbicyclo[2,2,2]octa-2,5-diene (28 mg), water (1.7 mL), and di-μ-chlorotetraethylene dirhodium (I) (19 mg), followed by adding potassium hydroxide (39 mg); the resulting mixture was stirred under nitrogen at room temperature for one hour; then, the reaction was quenched with 30 mL saturated aqueous sodium bicarbonate solution. The product was extracted with ethyl acetate (3×60 mL); the combined organic extracts were washed with brine once and dried over anhydrous sodium sulfate; after filtering out the drying reagent, the filtrate was concentrated in vacuum; the resulting residue was purified on silica gel column with a mixture of 15/85 EtOAc/heptanes. It produced 0.91 g colorless oil with 93% purity (~63% yield); the ratio of (2S,3S)-/(2R,3S)-isomer is 63:37.

Example 6g

Synthesis of
(2R,3R)-3-(3-methoxyphenyl)-2-methylpentanal

To a reaction flask were charged 3-methoxyphenylboronic acid (0.5 g), trans-2-methyl-2-pentenal (0.37 g), MeOH (5 mL), THF (1.2 mL), (1S,4S)-2,5-diphenylbicyclo[2,2,2]octa-2,5-diene (14 mg), water (0.9 mL), and di-μ-chlorotetraethylene dirhodium (I) (9.5 mg), followed by adding potassium carbonate (45 mg); the resulting mixture was stirred under nitrogen at room temperature overnight; the reaction was quenched with 30 mL saturated aqueous sodium bicarbonate solution. The product was extracted with ethyl acetate (3×60 mL); the combined organic extracts were washed with brine once and dried over anhydrous sodium sulfate; after filtering out the drying reagent, the filtrate was concentrated in vacuum; the resulting residue was purified on silica gel column with a mixture of 15/85 EtOAc/heptanes. It produced 0.44 g colorless oil with 82% purity and 55% yield. The ratio of (2R,3R)-/(2S,3R)-isomers is 59:41 in the product.

Example 6h

Synthesis of
(2R,3R)-3-(3-methoxyphenyl)-2-methylpentanal

To a reaction flask were charged 3-methoxyphenylboronic acid (0.5 g), trans-2-methyl-2-pentenal (0.37 g), MeOH (5 mL), THF (1.2 mL), (1S,4S)-2,5-diphenylbicyclo[2,2,2]octa-2,5-diene (14 mg), water (0.9 mL), and di-μ-chlorotetraethylene dirhodium (I) (9.5 mg), followed by adding sodium phosphate (53 mg); the resulting mixture was stirred under nitrogen at room temperature overnight; then, the reaction was quenched with 30 mL saturated aqueous sodium bicarbonate solution. The product was extracted with ethyl acetate (3×60 mL); the combined organic extracts were washed with brine once and dried over anhydrous sodium sulfate; after filtering out the drying reagent, the filtrate was concentrated in vacuum; the resulting residue was purified on silica gel column with a mixture of 15/85 EtOAc/heptanes. It produced 0.51 g colorless oil with 84% purity and yield=64%. The ratio of (2R,3R)-/(2S,3R)-isomers is 58:42.

Example 6i

Synthesis of
(2S,3S)-3-(3-methoxyphenyl)-2-methylpentanal

To the reaction flask under nitrogen was charged with 3-methoxyphenylboronic acid(10 g), trans-2-methyl-2-pentanal(7.35 g), methanol(100 mL), tetrahydrofuran(24 mL), water (17 mL), (1R,4R)-2,5-diphenylbicyclo[2,2,2]octa-2,5-diene(280 mg), di-μ-chlorotetraethylene dirhodium(I) (190 mg), followed by adding potassium hydroxide powder(390 mg). The resulting mixture was stirred under nitrogen at room temperature for five hrs. The reaction was quenched by adding 150 mL saturated ammonium chloride aqueous solution. The product was extracted with ethyl acetate (3×150 mL). The combined organic extracts were washed with aqueous ammonium chloride once, brine once and dried over sodium sulfate. The drying reagent was filtered; the filtrate was concentrated in vacuum; the residue was purified on silica gel column with a mixture of 1:9 EtOAc/hexane mixture as elute; the collected fractions were evaporated in vacuum and it gave 9.9 g colorless oil with 74.8% purity and 55% yield; the ratio of (2S,3S)-/(2R,3S)-isomers is 63:37 in the product.

Example 6j

Synthesis of
(2S,3S)-3-(3-methoxyphenyl)-2-methylpentanal

To the reaction flask under nitrogen was charged with 3-methoxyphenylboronic acid(10 g), trans-2-methyl-2-pentanal (7.5 g), methanol (100 mL), tetrahydrofuran(24 mL), water (17 mL), (1R,4R)-2,5-diphenylbicyclo[2,2,2]octa-2,5-diene (285 mg), di-μ-chlorotetraethylene dirhodium(I) (190 mg), followed by adding sodium phosphate powder(6.6 g). The resulting mixture was stirred under nitrogen at room temperature overnight. The reaction was quenched by adding 300 mL 0.5 N hydrochloric acid aqueous solution. The product was extracted with ethyl acetate (3×150 mL). The combined organic extracts were washed with brine once and dried over sodium sulfate. The drying reagent was filtered; the filtrate was concentrated in vacuum; the residue was purified on silica gel column with a mixture of 5:95 EtOAc/ hexane mixture as elute; the collected fractions were evaporated in vacuum and it gave the titled compound as colorless oil with 78% purity and 63% yield.

Example 6k

Synthesis of (2R,3R)-2-Methyl-3-(3-Methoxyphenyl)pentanal

To a reaction flask were charged 3-methoxyphenylboronic acid (1.0 g), trans-2-methyl-2-pentenal (0.73 g), MeOH (9.8 mL), THF (2.4 mL), (1S,4S)-2,5-diphenylbicyclo[2,2,2]octa-2,5-diene (28 mg), water (1.7 mL), and di-μ-chlorotetraethylene dirhodium(I) (19 mg), followed by adding potassium hydroxide (39 mg); the resulting mixture was stirred under nitrogen at room temperature for one hour; then, the reaction was quenched with 30 mL saturated aqueous sodium bicarbonate solution. The product was extracted with ethyl acetate (3×60 mL); the combined organic extracts were washed with brine and dried over anhydrous sodium sulfate; after filtering out the drying reagent, the filtrate was concentrated under vacuum; the resulting residue was purified on silica gel column with a mixture of 15/85 EtOAc/heptanes. It produced 0.91 g colorless oil, yield=63%. The ratio of (2R,3R)-/(2S,3R)-isomers was 63/37 in the final product.

Example 6l

Synthesis of 3-(3-methoxyphenyl)-2-methylpentanal from methoxypenylboroxin

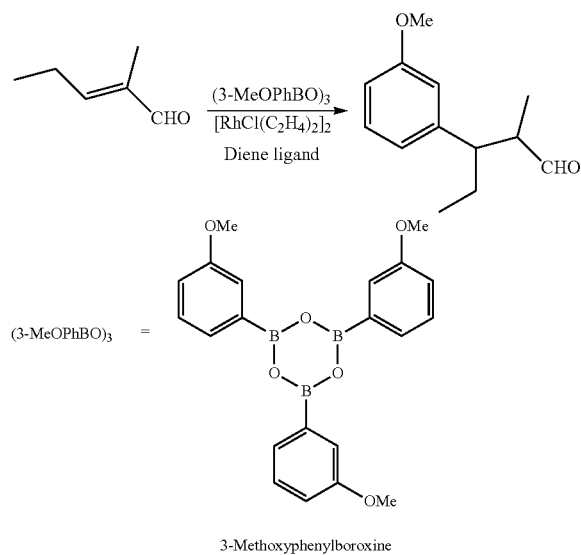

To a reaction flask were charged (1S,4S)-2,5-diphenylbicyclo[2,2,2]octa-2,5-diene (5.8 mg), di-μ-chlorotetraethylene dirhodium (I) (3.8 mg), 3-methoxyphenylboroxine (0.19 g), trans-2-methyl-2-pentenal (0.15 g), and 2.5 mL mixture of MeOH/THF(2:0.5); the resulting mixture was stirred at room temperature under nitrogen for 11 minutes; 0.36 mL of potassium hydroxide aqueous solution (pH=12.94) was added. The resulting yellow solution was stirred at room temperature overnight. The reaction produced desired 3-(3-methoxyphenyl)-2-methylpentanal in 81% integration area under LC analysis; the ratio of (2R,3R)-/(2S,3R)-isomers is 68:32 in the product.

Example 6m

Synthesis of 3-(3-methoxyphenyl)-2-methylpentanal from methoxypenylboroxin

To a reaction flask were charged (1S,4S)-2,5-diphenylbicyclo[2,2,2]octa-2,5-diene (5.8 mg), di-μ-chlorotetraethylene dirhodium (I) (3.8 mg), 3-methoxyphenylboroxine (0.19 g), trans-2-methyl-2-pentenal (0.15 g), and 2.5 mL mixture of MeOH/THF(2:0.5); the resulting mixture was stirred at room temperature under nitrogen for 11 minutes; 0.36 mL of potassium hydroxide aqueous solution (pH=12.94) was added. The resulting yellow solution was stirred at room temperature overnight. The reaction produced desired 3-(3-methoxyphenyl)-2-methylpentanal in 84% integration area under LC analysis; the ratio of (2R,3R)-/(2S,3R)-isomers is 68:32 in the product.

Example 6n

Synthesis of 3-(3-methoxyphenyl)-2-methylpentanal from potassium 3-methoxyphenyl trifluoroborate To the reaction flask was charged with (1S,4S)-2,5-diphenylbicyclo[2,2,2]-2,5-diene (5.7 mg), di-μ-chlorotetraethylene dirhodium(I) (3.8 mg), potassium 3-methoxyphenyl trifluoroborate(0.28 g), methanol/tetrahydrofuran mixture (2.5 mL with 2:0.5 methanol/THF), and trans-2-methyl-2-pentenal(0.15 g). The resulting mixture was stirred at room temperature under nitrogen for 11 min; then to the reaction was added 0.36 mL potassium hydroxide aqueous solution with pH=12.94. The resulting mixture was stirred overnight. The reaction was quenched by adding 1.0 N HCl aqueous solution; the product was extracted with ethyl acetate; the combined organic extracts were washed with brine and dried over anhydrous sodium sulfate. After filtered the drying reagent, the filtrate was concentrated in vacuum; the residue was passed through a short silica gel column with a mixture of 5:95 Ethyl Acetate/Heptane mixture as eluent; the elute was collected and concentrated in vacuum; it provided 10 mg oil residue with 25% area purity on LC and 40:60 ratio of (2R,3R)-/(2S,3R)-isomers. GC-MS: MW$^+$=206.17 (first peak) 206.16 (second peak).

Example 6o

Synthesis of 3-(3-methoxyphenyl)-2-methylpentanal from potassium 3-methoxyphenylboronic acid pinacol ester To the reaction flask was charged with (1S,4S)-2,5-diphenylbicyclo[2,2,2]-2,5-diene (5.7 mg), di-μ-chlorotetraethylene dirhodium(I) (3.8 mg), 3-methoxypheylboronic acid pinacol ester (0.31 g), methanol/tetrahydrofuran mixture (2.5 mL with 2:0.5 methanol/THF), and trans-2-methyl-2-pentenal(0.15 g). The resulting mixture was stirred at room temperature under nitrogen for 11 min; then to the reaction was added 0.36 mL potassium hydroxide aqueous solution with pH=12.94. The resulting mixture was stirred overnight. The reaction was quenched by adding 1.0 N HCl aqueous solution; the product was extracted with ethyl acetate; the combined organic extracts were washed with brine and dried over anhydrous sodium sulfate. After filtered the drying reagent, the filtrate was concentrated in vacuum; the residue was purified through a silica gel column chromatograph with a mixture of 5:95 Ethyl Acetate/Heptane mixture as eluent; the elute was collected and concentrated in vacuum; it provided 70 mg oil residue with 98% area purity on LC and 62:38 ratio of (2R,3R)-/(2S,3R)-isomers. GC-MS: MW⁺=206.14 (first peak) and 206.19 (second peak).

Example 6p

Synthesis of 3-(3-methoxyphenyl)-2-methylpentanal with chiral purity

To a reaction flask were charged with (1S,4S)-2,5-diphenylbicyclo[2,2,2]octa-2,5-diene (11.4 mg), di-μ-chlorotetraethylene dirhodium (I) (7.6 mg), 3-methoxyphenyl-boronic acid (0.4 g), a mixture of methanol/tetrahydrofuran (5 mL, 2.0:0.5 MeOH/THF), trans-2-methyl-2-pentenal (0.3 g). The resulting mixture was stirred at room temperature under nitrogen for 11 minutes. A potassium hydroxide aqueous solution (0.76 mL, pH=12.94) was added. The resulting mixture was stirred for six hours. The reaction was quenched by adding 1.0 N hydrochloric acid aqueous solution. The product was extracted with ethyl acetate and washed with brine, then dried over anhydrous sodium sulfate. After filtering the drying reagent, the filtrate was concentrated in vacuum; it produced a yellow oil residue. The crude product was further purified on silica gel column eluted with ethyl acetate/heptane mixture. It gave 0.33 g colorless oil. Chiral analysis on UPC2 indicated the product had 63.7% chiral purity; the de=27.5%. The ratio of (2R,3R)-/(2S,3R)-isomers was 64/36.

Example 7

Preparation of 2-Methyl-3-(-3-Methoxyphenyl)pentanal in the Presence of an Amine Trans-2-methyl-2-pentenal and 3-methoxyphenylboronic acid were reacted in the presence of a proton acceptor and amine via catalytic asymmetric 1,4-addition reaction.

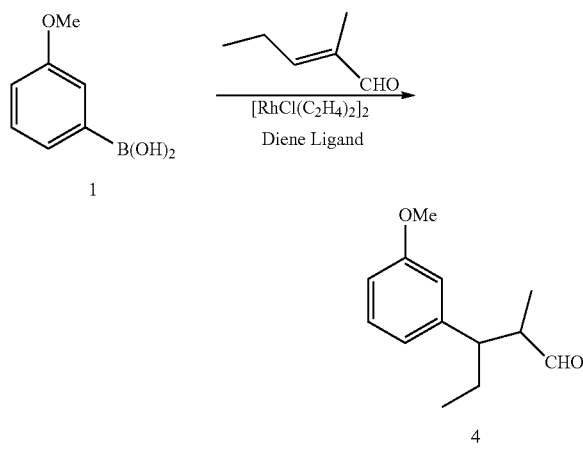

Example 7a

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol/tetrahydrofuran mixture (2:0.5), followed by adding trans-2-methyl-2-pentenal (0.15 g). The resulting mixture was stirred at room temperature under nitrogen for 11 min. To the reaction was added 4-methylmorpholine (14.5μL, 0.1 equivalents). The resulting mixture was stirred under nitrogen at room temperature overnight. The reaction produced the desired product with 37.5% area purity by LC. The ratio of (2R,3R)-isomer/(2S,3R)-isomer was 85:15 by GC analysis.

Example 7b

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol/tetrahydrofuran mixture (2:0.5), followed by adding trans-2-methyl-2-pentenal (0.15 g). The resulting mixture was stirred at room temperature under nitrogen for 11 min. To the reaction was added 4-methylmorpholine (116 μL, 0.8 equivalents). The resulting mixture was stirred under nitrogen at room temperature three hours. The reaction produced the desired product with 42.0% area purity by LC. The ratio of (2R,3R)-isomer/(2S,3R)-isomer was 86:14 by GC analysis.

Example 7c

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol/tetrahydrofuran mixture (2:0,5), followed by adding trans-2-methyl-2-pentenal (0.15 g). The resulting mixture was stirred at room temperature under nitrogen for 11 min, and then cooled to 0° C. in ice bath for 2 minutes. To the cooled reaction was added 4-methyl morpholine (29 μL, 0.2 equivalents). The resulting mixture was stirred under nitrogen at 0° C. for seven hours. The reaction produced the desired product with 21.4% area purity by LC. The ratio of (2R,3R)-isomer/(2S,3R)-isomer was 86:14 by GC analysis.

Example 7d

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol/tetrahydrofuran mixture (2:0.5), followed by adding trans-2-methyl-2-pentenal (0.15 g). The resulting mixture was stirred at room temperature under nitrogen for 11 min, and then warmed to 50° C. To the warmed reaction was added 4-methylmorpholine (29μL, 0.2 equivalents). The resulting mixture was stirred under nitrogen at 50° C. for one hour. The reaction produced the desired product with 52.5% integrated area by LC. The ratio of (2R,3R)-isomer/(2S,3R)-isomer is 85:15 by GC analysis.

Example 7e

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol, followed by adding trans-2-methyl-2-pentenal (0.15 g). The resulting mixture was stirred at room temperature under nitrogen for 11 min. To the reaction was added 4-methylmorpholine (29μL, 0.2 equivalents). The resulting mixture was stirred under nitrogen overnight. The reaction produced the desired product with 53% integrated area by LC. The ratio of (2R,3R)-isomer/(2S,3R)-isomer is 86:14 by GC analysis.

Example 7f

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.5 mL methanol, followed by adding trans-2-methyl-2-pentenal (0.15 g), The resulting mixture was stirred at room temperature under nitrogen for 11 min. To the reaction was added water (0.5 mL) and 4-methylmorpholine (29 μL, 0.2 equivalents). The resulting mixture was stirred under nitrogen at room temperature overnight. The reaction produced the desired product with 75.0% area purity by LC. The ratio of (2R,3R)-isomer/(2S,3R)-isomer was 85:15 by GC analysis.

Example 7g

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.1 mL methanol, followed by adding trans-2-methyl-2-pentenal (0.15 g). The resulting mixture was stirred at room temperature under nitrogen for 11 min. To the reaction was added water (0.9 mL) and 4-methylmorpholine (30μL, 0.2 equivalents). The resulting mixture was stirred under nitrogen at room temperature overnight. The reaction produced the desired product with 82.3% area purity by LC, the ratio of (2R,3R)-isomer/(2S,3R)-isomer was 86:14 by GC analysis.

Example 7h

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.1 mL methanol, followed by adding trans-2-methyl-2-pentenal (0.2 g, 1.5 equivalents). The resulting mixture was stirred at room temperature under nitrogen for 11 min. To the reaction was added water (0.9 mL) and 4-methylmorpholine (30μL, 0.2 equivalents). The resulting mixture was stirred under nitrogen at room temperature overnight. The reaction produced the desired product with 84.2% area purity by LC. The ratio of (2R,3R)-isomer/(2S,3R)-isomer is 86:14 by GC analysis.

Example 7i

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-dichlorotetraethylenedirhodium(I) (3.8 mg), 3-methoxyphenylboronic acid (0.2 g), 2.1 mL methanol, followed by adding trans-2-methyl-2-pentenal (0.2 g, 1.5 equivalents). The resulting mixture was stirred at room temperature under nitrogen for 11 min. To the reaction was added water (0.9 mL), N,N-dimethylformarnide (100 μL), and 4-methylmorpholine (30 μL, 0.2 equivalents). The resulting mixture was stirred under nitrogen at room temperature overnight. The reaction produced the desired product with 84.7% area purity by LC, the ratio of (2R,3R)-isomer/(2S,3R)-isomer was 86:14 by GC analysis.

Example 7j

Synthesis of (2R,3R)-3-(3-methoxyphenyl)-2-methylpentanal

To the reaction flask was charged with (1S,4S)-2,5-diphenylbicyclo[2,2,2]octa-2,5-diene (19 mg), di-μ-chlorotetraethylene dirhodium (I) (13 mg), 3-methoxyphenylboronic acid(2.0 g), methanol (20.25 mL), trans-2-methyl-2-pentenal(1.5 g). The resulting mixture was stirred under nitrogen at room temperature for 11 minutes; to the reaction was added water (9.75 mL), 4-methylmorpholine (0.3 mL), and potassium hydroxide (84 mg). The reaction was continued for 24 hours, it produced 84.1% product 2 based on HPLC area integration and the ratio of (2R,3R)-isomer/(2S,3R)-isomer was 84/16.

Example 7k

Synthesis of (2R,3R)-3-(3-methoxyphenyl)-2-methylpentanal

To the reaction flask was charged with (1S,4S)-2,5-diphenylbicyclo[2,2,2]octa-2,5-diene (19 mg), di-μ-chlorotetraethylene dirhodium (I) (13 mg), 3-methoxyphenylboronic acid(2.0 g), methanol (20.25 mL), trans-2-methyl-2-pentenal(1.5 g). The resulting mixture was stirred under nitrogen at room temperature for 11 minutes; to the reaction was added water (9.75 mL), 4-methylmorpholine (0.3 mL), and potassium hydroxide (170 mg). The reaction was continued for 23 hours, it produced 90.0% product 2 based on HPLC area integration and the ratio of (2R,3R)-isomer/(2S,3R)-isomer was 83/17 in the product.

Example 7l

Synthesis of (2R,3R)-3-(3-methoxyphenyl)-2-methylpentanal

To the reaction flask was charged with (1S,4S)-2,5-diphenylbicyclo[2,2,2]octa-2,5-diene (19 mg), di-μ-chlorotetraethylene dirhodium (I) (13 mg), 3-methoxyphenylboronic acid(2.0 g), methanol (20.25 mL), trans-2-methyl-2-pentenal(1.5 g). The resulting mixture was stirred under nitrogen at room temperature for 11 minutes; to the reaction was added water (9.75 mL), 4-methylmorpholine (0.3 mL), and potassium hydroxide (255 mg). The reaction was continued for 23 hours, it produced 90.0% product 2 based on HPLC area integration and the ratio of (2R,3R)-isomer/(2S,3R)-isomer was 79/21 in the product.

Example 7m

Synthesis of (2R,3R)-3-(3-methoxyphenyl)-2-methylpentanal

To the reaction flask was charged with (1S,4S)-2,5-diphenylbicyclo[2,2,2]octa-2,5-diene (95 mg), di-µ-chlorotetraethylene dirhodium (I) (65 mg), 3-methoxyphenylboronic acid(10.0 g), methanol (101 mL), trans-2-methyl-2-pentenal (15 g). The resulting mixture was stirred under nitrogen at room temperature for 15 minutes; to the reaction was added water (49 mL), 4-methyl morpholine (1.5 mL), and potassium hydroxide (850 mg). The reaction was continued for 23 hours; the reaction was quenched with 10% acetic acid aqueous solution (100 ml); the product was extracted with toluene (3×50 mL). The combined organic extracts were washed with brine (2×100 mL) and dried over anhydrous magnesium sulfate. After removing the drying reagent, the filtrate was concentrated in vacuum; it provided 12.2 light brown oil; LC analysis indicated the crude oil contained 91.8% product 2 (area integration); GC analysis indicated the ratio of (2R,3R)-isomer/(2S,3R)-isomer was 81.5/18.5.

Example 7n

Synthesis of (2R,3R)-3-(3-methoxyphenyl)-2-methylpentanal

To the reaction flask was charged with (1S,4S)-2,5-diphenylbicyclo[2,2,2]octa-2,5-diene (95 mg), di-µ-chlorotetraethylene dirhodium(I) (65 mg, 0.25% eqv), 3-methoxyphenylboronic acid (10 g), methanol(101 mL), 2-methyl-2-pentenal (7.5 g); the resulting mixture was stirred at room temperature under nitrogen for 15 minutes, then to the reaction was added water (49 mL), 4-methylmorpholine (3 mL). The resulting mixture was stirring at room temperature overnight; the reaction was cooled in ice bath and quenched by adding 15% acetic acid solution (100 mL). The resulting mixture was extracted with toluene (3×100 mL); the organic combined organic extracts were washed with brine (3×50 mL), and dried over magnesium sulfate (10 g). The drying reagent was filtered and washing with toluene (2×10 mL). The combined filtrates and washings were concentrated in vacuum; it provided 14.0 g crude product with 92.8% purity, the ratio of (2R,3R)-/(2S,3R)-isomers was 85.3/14.7.

Example 8

Preparation of 2-Methyl-3-(-3-Methoxyphenyl)pentanal in the Presence of Alternate Amines Trans-2-methyl-2-pentenal and 3-methoxyphenylboronic acid were reacted in the presence of a proton acceptor and an alternative amine via catalytic asymmetric 1,4-addition reaction.

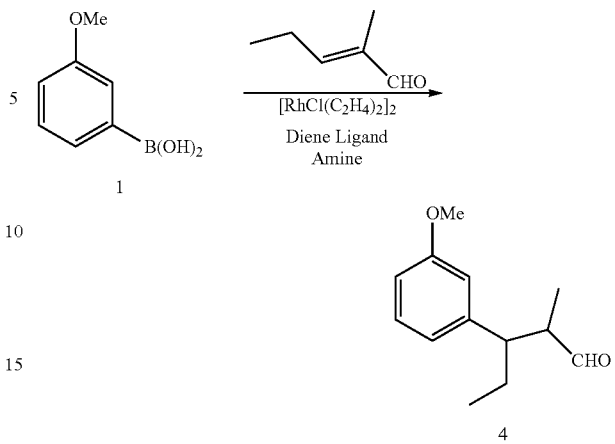

Example 8a

Synthesis of (2R,3R)-3-(3-methoxyphenyl)-2-methylpentanal

To a reaction flask were charged 3-methoxyphenylboronic acid (0.2 g), trans-2-methyl-2-pentenal (0.15 g), MeOH (2.0 mL), THF (0.48 mL), N,N-diisopropylethylamine (23 µL), (1S,4S)-2,5-diphenylbicyclo[2,2,2]octa-2,5-diene (5.6 mg), and di-µ-chlorotetraethylene dirhodium(I) (3.8 mg), water (1.7 mL); the resulting mixture was stirred under nitrogen at room temperature for one hour; then, the reaction was quenched with 30 mL saturated aqueous ammonium chloride solution. The product was extracted with ethyl acetate (3×60 mL); the combined organic extracts were washed with brine and dried over anhydrous sodium sulfate; after filtering out the drying reagent, the filtrate was concentrated under vacuum; the resulting residue was purified on silica gel column with a mixture of 15/85 EtOAc/heptanes. It produced 0.14 g colorless oil with 88% purity (area integration). The ratio of (2R,3R)-/(2S,3R)-isomers was 59/41 in the final product.

Example 8b

Synthesis of (2R,3R)-3-(3-methoxyphenyl)-2-methylpentanal

To five parallel reaction flasks were charged 3-methoxyphenylboronic acid (0.2 g), trans-2-methyl-2-pentenal (0.15 g), MeOH (2.0 mL), THF (0.48 mL), (1S,4S)-2,5-diphenylbicyclo[2,2,2]octa-2,5-diene (5.6 mg), and di-µ-chlorotetraethylene dirhodium(I) (3.8 mg), water (1.7 mL); after 5 minutes, to the reactions were added various amount of N,N-diisopropylethylamine, the resulting mixture was stirred under nitrogen at room temperature overnight; then, the reactions were sampled for analysis on HPLC and GC. The results were listed below: The products were then isolated as previously described.

| # | N,N-Diisopropylethyl amine | Product 2 (HPLC area integration) | Ratio of (2R,3R)/(2S,3R)-isomers (GC area integration) |
|---|---|---|---|
| 1 | 23 µL(10% equiv) | 59% | 60/40 |
| 2 | 46 µL(20% equiv) | 62% | 60/40 |

-continued

| # | N,N-Diisopropylethyl amine | Product 2 (HPLC area integration) | Ratio of (2R,3R)/(2S,3R)-isomers (GC area integration) |
|---|---|---|---|
| 3 | 92 μL(40% equiv) | 66% | 58/42 |
| 4 | 138 μL(60% equiv) | 68% | 58/42 |
| 5 | 184 μL(80% equiv) | 71% | 59/41 |

Example 8c

Synthesis of (2R,3R)-3-(3-methoxyphenyl)-2-methylpentanal

To a reaction flask were charged (1S,4S)-2,5-diphenylbicyclo[2,2,2]octa-2,5-diene (5.7 mg), di-μ-chlorotetraethylene dirhodium(I) (3.8 mg), 3-methoxyphenylboronic acid (0.2 g), trans-2-methyl-2-pentenal (0.15 g) and MeOH/tetrahydrofuran mixture (2:0.5, 2.5 mL); after the mixture was stirred under nitrogen at room temperature for 11 minutes, then to the reaction was added base (0.53 mmol); the resulting mixture was stirred under nitrogen at room temperature for seven hours, the reaction was sampled for HPLC and GC analysis. The analytical results were listed below. The products were then isolated as previously described.

| # | Bases | Product 2 (HPLC area integration) | Ratio of (2R,3R)/(2S,3R)-isomers (GC area integration) |
|---|---|---|---|
| 1 | (S)-α-Methylbenzylamine | 8.9% | 43/57 |
| 2 | (R)-α-Methylbenzylamine | 29.0% | 40/60 |
| 3 | Diethylamine | 86.1% | 76/24 |
| 4 | Dipropylamine | 22.0% | 54/46 |
| 5 | Diisopropylamine | 54.0% | 63/37 |
| 6 | Dibutylamine | 15.6% | 61/39 |
| 7 | Dipentylamine | 11.3% | 49/51 |
| 8 | Dicyclohexylamine | 85.0% | 65/35 |
| 9 | (S)-(−)-α,α-diphenyl-2-pyrrolidinemethanol trimethylsilyl ether | 30.6% | 75/25 |
| 10 | (R)-(+)-α,α-diphenyl-2-pyrrolidinemethanol trimethylsilyl ether | 16.0% | 69/31 |
| 11 | (S)-(−)-α,α-diphenyl-2-pyrrolidinemethanol | 5.0% | 74/26 |
| 12 | Pyrrolidine | 23.8% | 48/52 |
| 13 | Piperidine | 79.0% | 70/30 |
| 14 | 2-methylpiperidine | 84.3% | 73/27 |
| 15 | 2,5-dimethylpiperidine | 84.0% | 71/29 |
| 16 | 2,6-dimethylpiperidine | 45.7% | 67/33 |
| 17 | Piperazine | 2.8% | 67/33 |
| 18 | 2-Methylpiperazine | 2.1% | 54/46 |
| 19 | 2,6-dimethylpiperazine | 5.2% | 65/35 |
| 20 | morpholine | 14.3% | 75/25 |
| 21 | N-methylpyrrolidine | 61.7% | 73/27 |
| 22 | 4-methylmorpholine | 46.5% | 86/14 |
| 23 | 4-ethylmorpholine | 53.9% | 81/19 |
| 24 | N-methylpiperidine | 72.3% | 83/17 |
| 25 | 1,8-Diazabicyclo[5.4.0]undec-7-ene | 84.4% | 64/36 |
| 26 | N,N-diisopropylethylamine | 86.8% | 62/38 |
| 27 | Sodium t-Butoxide | 90.3% | 61/39 |
| 28 | triethylamine | 26.2% | 77/23 |

Example 9

Preparation of (3-(3-Methoxyphenyl)-N,N-2-trimethylpentan-1-amine (5)

The dimethylamino group was introduced at the aldehyde (4) via reductive-amination using dimethylamine and a hydride reducing agent.

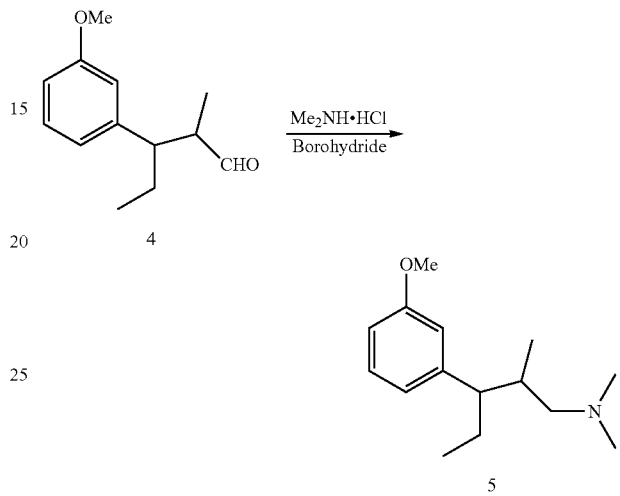

Example 9a

Synthesis of (2R,3R)- and (2S,3R)-3-(3-Methoxyphenyl)-N,N-2-trimethylpentan-1-amine To the reaction flask were added with 3-(3-methoxyphenyl)-2-methylpentanals (13 g with (2R,3R)-/(2S,3R)-isomers=58/42), tetrahydrofuran (280 mL), N,N-dimethylamine hydrochloride (5.2 g), N, N-diisopropylethylamine (10.6 mL), and sodium triacetoxyborohydride (28 g). The resulting mixture was stirred under nitrogen at room temperature for five hour, another portion of sodium triacetoxyborohydride (10 g) and diisopropylethylamine (2 mL) were added. The reaction continued overnight. Then the reaction was quenched by adding 150 mL 1.0 N sodium hydroxide aqueous solution. The resulting mixture was stirred at room temperature for 15 minutes. The product was extracted with 1:9 dichloromethane/toluene mixtures (3×150 mL). The combined organic phases were evaporated under vacuum until the volume became around 200 mL. The residue solution was then extracted with 1N HCl aqueous solution three times. The combined aqueous extracts were cooled in ice bath and then basified with 1.0 N sodium hydroxide aqueous solution to pH=10.0. The product was extracted with 1:9 dichloromethane/toluene (3×150 mL); the combined organic extracts were washed with brine and dried over anhydrous sodium sulfate. After filtering the drying reagent, the filtrate was concentrated under vacuum. The crude pink oil residue was purified on silica gel column with 0.3% diisopropylethylamine solution in 3:7 ethyl acetate/heptanes mixture. The collected fractions were evaporated under vacuum. The first fraction provided 2.6 g oil of (2S,3R)-3-(3-Methoxyphenyl)-N,N-2-trimethylpentan-1-amine with 99.4% purity based on HPLC. The second fraction provided 2.5 g oil of (2R,3R)-3-(3-Methoxyphenyl)-N,N-2-trimethylpentan-1-amine with 99.4% purity based on HPLC.

Example 9b

Synthesis of (2R,3S)- and (2S,3S)-3-(3-Methoxyphenyl)-N,N,2-trimethylpentan-1-amine To the reaction flask was added 3-(3-methoxyphenyl)-2-methylpentanals (9.9 g, the (2R,3S)-/(2S,3S)-isomers ratio was 63/37), dimethylformamide (260 mL), dimethylamine hydrochloride (12.6 g), N, N-diisopropylethylamine (30.8 mL), and sodium cyanoborohydride (11.2 g). The resulting mixture was stirred under nitrogen at room temperature for 6 hours; the reaction was quenched by adding 260 mL of saturated sodium bicarbonate aqueous solution. The product was extracted with 1:9 methanol/dichloromethane mixtures. The combined organic extracts were washed with saturated sodium bicarbonate aqueous solution and dried over anhydrous sodium sulfate. The drying reagent was then filtered and the filtrate was concentrated in vacuum. The residue was then purified on silica gel column with 0.5% diisopropylethylamine solution in 3:7 EtOAc/heptane mixtures. (2R,3S)-3-(3-methoxyphenyl)-N,N-2-trimethylpentan-1-amine was obtained in 0.63 g colorless oil with 97.5% purity on HPLC; (2S,3S)-3-(3-methoxyphenyl)-N,N-2-trimethylpentan-1-amine was obtained in 1.4 g colorless oil with 99.2% purity on HPLC.

Example 9c

Synthesis of (2R,3S)- and (2S,3S)-3-(3-Methoxyphenyl)-N,N,2-trimethylpentan-1-amine To the reaction flask was charged with dimethylamine hydrochloride (5.84 g), crude 3-(3-methoxyphenyl)-2-methylpentanal(14.0 g, 92.8%), and 2-propanol (166 mL); the resulting mixture was stirred at room temperature under nitrogen for 10 min; then to the reaction was added sodium triacetoxyborohydride (19 g). The resulting mixture was stirred at room temperature overnight; the reaction was quenched by adding water (60 mL). After stirring for 15 minutes, the mixture was concentrated in vacuum to remove 2-propanol. The aqueous residue was cooled to 0° C. in ice bath and 40 mL 6 N HCl was added; then resulting solution was extracted with toluene (4×40 mL) to remove impurities. The aqueous residue was again cooled to 0° C. in ice bath and was basified with 10% NaOH solution until pH=11 to 12. The product was extracted with toluene (3×100 mL). The combined organic extracts were dried over magnesium sulfate (10 g), the filtrate was concentrated in vacuum and provided 13.3 g oil as crude product with 81% purity.

Example 10

Preparation of 3-(3-hydroxyphenyl)-N,N,2-trimethylpentan-1-amine (6)

A final O-demethylation on the amine compound (5) yielded the phenol (6).

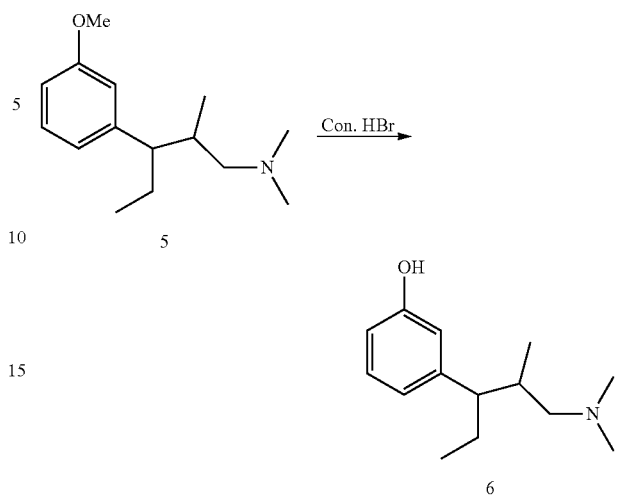

Example 10a

Synthesis of (2R,3R)-3-(3-hydroxyphenyl)-N,N-2-trimethylpentan-1-amine. HCl (tapentadol HCl salt)

To the reaction flask was charged with (2R,3R)-3-(3-methoxyphenyl)-N,N-2-trimethylpentan-1-amine (3.44 g) and 50 ml 48% hydrobromic acid under nitrogen. The resulting light brown solution was heated to 100° C. for three hours; another 10 mL of 48% hydrobromic acid was added. After the reaction continued at 100° C. for another 1.5 hours, the reaction was cooled to 0° C. in ice bath, the pH of the reaction was adjusted to 8 with sodium bicarbonate. The product was then extracted with 1:9 methanol/dichloromethane. The combined organic extracts were washed with aqueous sodium bicarbonate solution, dried over anhydrous sodium sulfate. The drying reagent was filtered, the filtrate was concentrated in vacuum; the oil residue was dissolved in 30 mL methanol; the resulting solution was cooled in ice bath and then to the cooled solution was added 48 mL of 0.5 N HCl aqueous solution. The resulting solution was concentrated under vacuum. The residue was dissolved in 150 mL 2-propanol. To the resulting solution was added 0.29 g active carbon. The resulting mixture was heated at 80° C. for 5 min; then the active carbon was filtered via celite and washed with hot 2-propanol. The combined filtrate and washings were concentrated under vacuum, plenty of white solid were precipitated. The mixture was further stirred in ice bath for 15 min, then the precipitates were collected by filtration and washed with ice cold 2-propanol; after dried in air, the product was further dried in vacuum oven at 60° C. overnight. It provided 2.31 g white solid with 96.6% optical purity on chiral HPLC.

Example 10b

Synthesis of (2S,3R)-3-(3-hydroxyphenyl)-N,N-2-trimethylpentan-1-amine HCl

To the reaction flask was charged with (2S,3R)-3-(3-methoxyphenyl)-N,N-2-trimethylpentan-1-amine (2.6 g) and 50 mL 48% hydrobromic acid. The resulting solution was heated to 110° C. for four hours. Then the reaction was cooled to 0° C. in ice bath, the pH of the reaction was then adjusted to 8 with sodium bicarbonate. The product was extracted with 1:9 methanol/dichloromethane mixtures. The combined organic phase was dried over anhydrous sodium sulfate. After filtering the drying reagent, the filtrate was evaporated to a light brown oil residue in vacuum. To the residue was added 100 mL of 0.5 N HCl solution in 1:1 water/2-propanol mixture. After stirring 15 minutes, the solution was evaporated in vacuum; the residue was dissolved in 50 mL 2-propanol; to the resulting solution was added 0.15 g active carbon. The resulting mixture was heated to 80° C. for 30 min. The mixture was filtered through celite and washed with hot 2-propanol. The combined filtrate and washings were evaporated in vacuum. The residue was dissolved in 21 mL 2-butanone; the resulting mixture was heated to reflux; to the refluxing mixture was added slowly methanol until the mixture became clear solution. After refluxing 10 minutes, the solution was concentrated under vacuum, plenty of precipitates were formed. The mixture was then stirred at room temperature overnight; the solid was collected by filtration and washed with ice cold 2-propanol. After dried in air, the solid was further dried in vacuum oven at 60° C. overnight, it provided 1.6 g solid with 99.5% optical purity based on chiral HPLC.

Example 10c

Synthesis of (2R,3S)-3-(3-hydroxyphenyl)-N,N-2-trimethylpentan-1-amine HCl

To the reaction flask was added with (2R,3S)-3-(3-methoxyphenyl)-N,N,-2-trimethylpentan-1-amine (1.0 g) and 20 mL 48% hydrobromic acid. The resulting solution was heated to 110° C. for two hours. After the reaction was cooled to 0° C. in ice bath, pH of the reaction mixture was adjusted to 8 with sodium bicarbonate. The product was extracted with 1:9 methanol/dichloromethane. The combined organic extracts were dried over anhydrous sodium sulfate. The drying reagent was filtered; the filtrate was concentrated in vacuum and it provided crude light yellow oil. The light yellow oil was dissolved in 20 mL methanol; the resulting solution was cooled in ice bath, to the cooled solution was added 20 mL 0.5 N HCl aqueous solution. The mixture was then stirred in ice bath for 15 minutes, and then concentrated in vacuum to provide a light yellow oil. To the yellow oil was added 20 mL methanol, followed by adding 0.15 g active carbon. The resulting mixture was heated for refluxing for 15 minutes. The active carbon was filtered through a layer of celite and washed with hot methanol. The combined filtrate and washings were concentrated in vacuum. The residue was crystallized from 2-butanone/methanol mixture. The collected crystals were dried in vacuum oven at 60° C. overnight, it provided 0.83 g solid with 99.0% optical purity based on chiral HPLC.

Example 10d

Synthesis of (2S,3S)-3-(3-hydroxyphenyl)-N,N-2-trimethylpentan-1-amine HCl

To the reaction flask was added 1.4 g (2S,3S)-3-(3-methoxyphenyl)-N,N-2-trimethylpentan-1-amine and 20 mL 48% hydrobromic acid. The resulting mixture was heated to 100° C. (oil bath temperature) for five hours, then cooled to 0° C. in ice bath; pH of the reaction was adjusted to 8 with sodium bicarbonate. The product was extracted with 1:9 dichloromethane/heptanes mixture. The combined organic extracts were washed with saturated sodium bicarbonate solution, dried over anhydrous sodium sulfate. After filtered the drying reagent, the filtrate was concentrated under vacuum. The residue was dissolved in 30 mL methanol and then cooled in ice bath; to the cooled solution was added 15 mL of 0.5 N hydrochloric acid solution. After stirring for 15 minutes, the solution was concentrated under vacuum. The residue was dissolved in 2-propanol and then treated with active carbon. After filtering the active carbon through celite, the filtrate was concentrated in vacuum. The residue was re-crystallized from 2-butanone. The harvested product was dried in vacuum oven at 60° C. overnight, it provided 1.4 g off-white solid with 98.5% optical purity based on chiral HPLC.

Example 10e

Synthesis of (2R,3R)-3-(3-hydroxyphenyl)-N,N-2-trimethylpentan-1-amine HCl. (tapentadol HCl salt)

To the reaction flask was charged with O-methyl tapentadol (13.7 g), methane sulfonic acid (60 mL), and dl-methionine (9.5 g) was added. The reaction mixture was stirred at a temperature of 90° C. for 19 hours, and then cooled to 0° C. in ice bath. The pH was adjusted with ice cold 35% NaOH aqueous solution to a pH of approximately 12. The product was extracted with EtOAc (3×60 mL). The combined organic extracts were treated with active carbon (0.3 g) at room temperature for two hours. The active carbon was filtered; the filtrate was concentrated in vacuum. To the residue was added 35 mL methanol, and then to the resulting solution was added 90 mL ice cold 10% HCl in isopropanol. After stirring for 5 minutes, the mixture was heated to 70° C. for 5 minutes, and then cooled to room temperature; ~1 mg of seed crystals was added. The mixture was then concentrated on a rotary evaporator at 30° C. (water bath) until the volume reached ~40 mL; plenty of solid formed during the concentration. The mixture was then rotated on a rotary evaporator at room temperature and at ambient temperature for two hour. The solid was filtered and washed with isopropanol. Then solid was further recrystallized from a mixture of isopropanol and methanol. It provided 9.6 g tapentadol hydrochloric salt with 99.4% area purity.

What is claimed is:

1. A process for preparing a compound of Formula (VI), the process comprising:

a) contacting a compound of Formula (I) with a compound of Formula (VIII) in the presence of a transition metal catalyst and a chiral ligand to form a compound of Formula (IX);

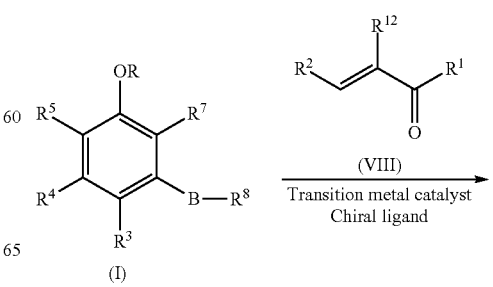

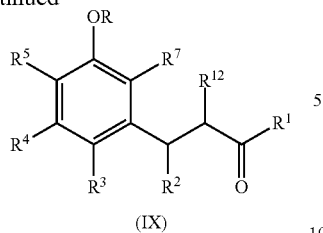

(IX)

b) contacting the compound of Formula (IX) with a secondary amine having Formula (X) to form a compound of Formula (V); and

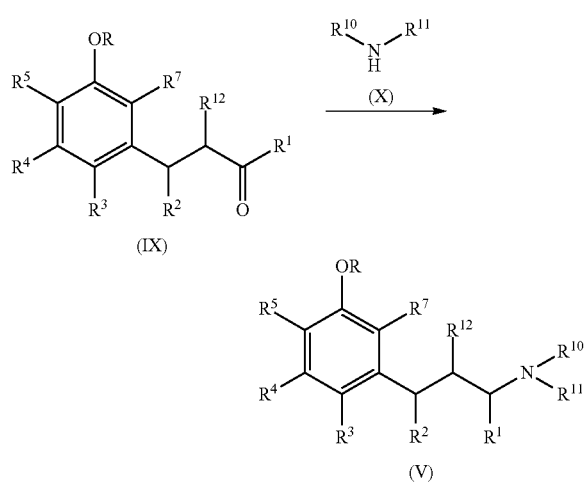

c) contacting the compound of Formula (V) with an O-dealkylating agent to form the compound of Formula (VI),

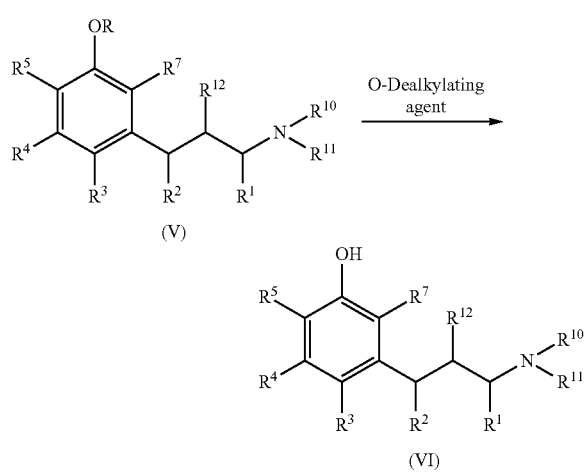

wherein:
R is alkyl or alkyl substituted with other than aryl;
$R^1$ is hydrogen, alkyl, or substituted alkyl;
$R^2$ is hydrocarbyl or substituted hydrocarbyl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl;

$R^8$ is

—O—$(CR^{13}R^{14})_n$—O—, or trihalo;
$R^{10}$ and $R^{11}$ are independently hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{12}$ is hydrocarbyl or substituted hydrocarbyl;
$R^{13}$ and $R^{14}$ are independently hydrogen, hydrocarbyl, substituted hydrocarbyl, or boron containing moiety;
$R^{20}$ and $R^{21}$ are independently hydrogen, hydrocarbyl, or substituted hydrocarbyl; and
n is an integer of 1 or greater.

2. The process of claim 1, wherein $R^1$ is hydrogen, alkyl, or substituted alkyl; $R^2$ is alkyl or substituted alkyl; $R^3$, $R^4$, $R^5$, and $R^7$ are independently hydrogen, alkyl, substituted alkyl, hydroxyl, alkoxy, substituted alkoxy, aryl, substituted aryl, alkylaryl, or substituted alkylaryl; $R^{10}$ and $R^{11}$ are independently alkyl or substituted alkyl; and $R^{13}$ and $R^{14}$ are independently hydrogen, alkyl, aryl, or alkylaryl.

3. The process of claim 2, wherein $R^1$ is $C_1$-$C_{10}$ alkyl; $R^2$ is $C_1$-$C_{10}$ alkyl; $R^3$, $R^4$, $R^5$, and $R^7$ are hydrogen; and $R^{10}$, $R^{11}$ and $R^{12}$ are $C_1$-$C_{10}$ alkyl.

4. The process of claim 1, wherein R is methyl; $R^1$ is hydrogen; $R^2$ is ethyl; each of $R^3$, $R^4$, $R^5$, and $R^7$ is hydrogen; and $R^{10}$, $R^{11}$, and $R^{12}$ are methyl.

5. The process of claim 1, wherein the compound of Formula (I), the compound of Formula (VIII), and the transition metal catalyst are present at a molar ratio of about 1:0.5:0.001 to about 1:2.0:0.05; and step (a) is conducted at a temperature from about −10° C. to about 80° C.

6. The process of claim 5, wherein the transition metal catalyst is a transition metal complex chosen from a rhodium complex, a palladium complex, or a ruthenium complex; the chiral ligand is a bicyclic chiral diene; and the transition metal catalyst and the chiral ligand are present at a weight ratio of about 1:0.1 to about 1:10.

7. The process of claim 6, wherein the compound of Formula (IX) is obtained with a diastereomeric excess of at least about 60%.

8. The process of claim 6, wherein step (a) further comprises contact with an amine, the amine being secondary, tertiary, chiral, or achiral.

9. The process of claim 8, wherein the compound of Formula (I) and the amine are present at a molar ratio of about 1:0.01 to about 1:1.0.

10. The process of claim 9, further comprising contact with a proton acceptor.

11. The process of claim 10, wherein the compound of Formula (I) and the proton acceptor are present at a molar ratio of about 1:0.01 to about 1:2.

12. The process of claim 11, wherein the compound of Formula (IX) is obtained with a diastereomeric excess of at least about 70%.

13. The process of claim 1, wherein the compound of Formula (IX) and the compound of Formula (X) are present at a molar ratio of about 1:0.5 to about 1:60; and step (b) is conducted at a temperature of about 0° C. to about 80° C.

14. The process of claim 13, further comprising contact with a reducing agent.

15. The process of claim 14, wherein the compound of Formula (IX) and the reducing agent are present at a weight ratio of about 1:0.3 to about 1:5.

16. The process of claim 1, wherein the O-dealkylating agent and the compound of Formula (V) are present at weight ratio of about 1:1 to about 400:1; and step (c) is conducted at a temperature of about 50° C. to about 200° C.

17. The process of claim 1, wherein the compound of Formula (I) is m-methoxyphenylboronic acid, 3-methoxyphenyl trifluoroborate, 3-methoxyphenylboronic acid pinacol ester, 3-methoxyphenylboronic ester, or is derived from 3-methoxyphenylboroxine; the compound of Formula (VIII) is trans-2-methyl-2-pentenal; the transition metal catalyst is [RhCl($C_2H_4$)$_2$]$_2$; the chiral ligand is (1S,4S)-2,5-diphenylbicyclo[2,2,2]octa-2,5-diene; the compound of Formula (X) is dimethylamine; the O-dealkylating agent is a hydrogen halide; and the compound of Formula (VI) is 3-[(1R,2R)-3-(dimethyamino)-1-ethyl-2-methylpropyl]phenol.

18. The process of claim 17, wherein step (a) further comprises contact with an amine and, optionally, a proton acceptor; the amine being 4-methylmorpholine.

19. The process of claim 18, wherein the compound of Formula (I), the compound of Formula (VII), the transition metal catalyst, the chiral ligand, the amine, and the optional proton acceptor are present at a molar ratio of 1:1.15:0.007:0.4:0.2; step (a) is conducted at a temperature of about 23° C. and under nitrogen; the compound of Formula (IX) and the compound of Formula (X) are present at a molar ratio of about 1:1; step (b) is conducted in the presence of a reducing agent, at a temperate of about 23° C., and under nitrogen; the O-dealkylating agent and the compound of Formula (V) are present at a weight ratio of about 26:1; and step (c) is conducted at a temperature of about 110° C. and under nitrogen.

20. The process of claim 19, wherein the compound of Formula (VI) has a yield of at least about 30%.

* * * * *